(12) United States Patent
Udaka et al.

(10) Patent No.: US 7,037,684 B2
(45) Date of Patent: May 2, 2006

(54) PROCESS FOR PRODUCING POLYPEPTIDE HAVING DISULFIDE BOND

(75) Inventors: Shigezo Udaka, 24-3, Uesono-cho 1-chome, Meito-ku, Nagoya, Aichi (JP); Seiji Sato, Ibaraki (JP); Toshiyuki Kudo, Ibaraki (JP); Shusaku Oka, Ibaraki (JP); Naohiko Higashikuni, Ibaraki (JP); Masaaki Kondo, Ibaraki (JP)

(73) Assignees: Itoham Foods Inc., Koba (JP); Shigezo Udaka, Nagoya (JP)

( * ) Notice: Subject to any disclaimer, the term of this patent is extended or adjusted under 35 U.S.C. 154(b) by 199 days.

(21) Appl. No.: 10/221,677

(22) PCT Filed: Mar. 13, 2001

(86) PCT No.: PCT/JP01/01987

§ 371 (c)(1),
(2), (4) Date: Sep. 13, 2002

(87) PCT Pub. No.: WO01/68884

PCT Pub. Date: Sep. 20, 2001

(65) Prior Publication Data

US 2004/0018596 A1    Jan. 29, 2004

(30) Foreign Application Priority Data

Mar. 14, 2000    (JP) .............................. 2000-070753

(51) Int. Cl.
| | |
|---|---|
| *C07H 21/04* | (2006.01) |
| *C12P 21/04* | (2006.01) |
| *C12N 1/20* | (2006.01) |
| *C12N 15/00* | (2006.01) |
| *A61K 38/28* | (2006.01) |

(52) U.S. Cl. .................. 435/69.4; 435/69.8; 435/69.7; 435/69.1; 435/232; 435/320.1; 435/252.3; 435/252.31; 536/23.2; 536/23.5; 536/23.4; 530/303

(58) Field of Classification Search ................ 435/232, 435/320.1, 252.3, 252.31, 69.1, 69.8, 69.7, 435/69.4; 536/23.2, 23.4, 23.5; 530/303
See application file for complete search history.

(56) References Cited

U.S. PATENT DOCUMENTS 6,291,205 B1 *    9/2001    Tuite et al. ................ 435/69.1

FOREIGN PATENT DOCUMENTS

| EP | 0 509 841 | 10/1992 |
| EP | 0 955 370 | 11/1999 |
| JP | 6-38771 | 2/1994 |
| WO | 93/25676 | 12/1993 |
| WO | 97 38123 | 10/1997 |
| WO | 00 66738 | 11/2000 |

OTHER PUBLICATIONS

Winter et al., J. Biotechnol. 84:175-185, 2000.*
A. Miyauchi et al.: "Pilot scale production of a recombinant human epidermal growth factor, secreted by *Bacillus brevis*, using expanded bed adsorption" J. Indust. Microbiol. Biotech., vol. 21, pp. 208-214 1998.
Tsutomu Kajino et al.: "A protein disulfide isomerase gene fusion expression productivity of *Bacillus brevis*" Applied and Environmental Microbiology, vol. 66, No. 2, pp. 638-642 Feb. 2000.
Hideaki Tojo et al.: "Production of human protein disulfide isomerase by *Bacillus brevis*" Journal of Biotechnology, vol. 33, No. 1, pp. 55-62 1994.
S. Udaka et al.: "High-level secretion of heterologous proteins by *Bacillus brevis*" Methods in Enzymology, vol. 217, pp. 23-33 1993.

* cited by examiner

*Primary Examiner*—Rebecca E. Prouty
*Assistant Examiner*—Delia M. Ramirez
(74) *Attorney, Agent, or Firm*—Oblon, Spivak, McClelland, Maier & Neustadt, P.C.

(57) ABSTRACT

The invention relates to a DNA that enables co-expression of a protein disulfide isomerase and a polypeptide having disulfide bonds. The invention further relates to a process of producing polypeptides using the DNA and a process of enhancing the efficiency of formation of correct disulfide bond in an expression system of a gene recombinant polypeptide having disulfide bonds.

18 Claims, 15 Drawing Sheets

Fig. 1A

MWPsp-MWPmp9-GSLQPR-Bchain-RGHRP-Linker-PR-Achain

1 GTC GTT AAC AGT GTA TTG GCT AGT GCA CTC GCA CTT ACT GTT GCT CCA 48
1 Val Val Asn Ser Val Leu Ala Ser Ala Leu Ala Leu Thr Val Ala Pro 16

49 ATG GCT TTC GCA GCA GAA GAA GCA GCA ACT ACT ACA GCT GGG TCC CTG 96
17 Met Ala Phe Ala Ala Glu Glu Ala Ala Thr Thr Thr Ala Gly Ser Leu 32

97 CAG CCA CGT TTT GTG AAC CAA CAC CTG TGC GGC TCA CAC CTG GTG GAA 144
33 Gln Pro Arg Phe Val Asn Gln His Leu Cys Gly Ser His Leu Val Glu 48

145 GCT CTC TAC CTA GTG TGC GGG GAA AGA GGC TTC TTC TAC ACA CCC AAG 192
49 Ala Leu Tyr Leu Val Cys Gly Glu Arg Gly Phe Phe Tyr Thr Pro Lys 64

193 ACC CGC GGT CAC CGT CCA GAG GCA GAG GAC CTG CAG GTG GGG CAG GTG 240
65 Thr Arg Gly His Arg Pro Glu Ala Glu Asp Leu Gln Val Gly Gln Val 80

Continued from Fig. 1A

```
241 GAG CTG GGC GGG GGC CCT GGT GCA GGC AGC CTG CAG CCC TTG GCC CTG 288
 81 Glu Leu Gly Gly Gly Pro Gly Ala Gly Ser Leu Gln Pro Leu Ala Leu  96

289 GAG GGG TCC CTG CAG CCA CGT GGC ATT GTG GAA CAA TGC TGT ACC AGC 336
 97 Glu Gly Ser Leu Gln Pro Arg Gly Ile Val Glu Gln Cys Cys Thr Ser 112

337 ATC TGC TCC CTC TAC CAG CTG GAG AAC TAC TGC AAC TAG              375
113 Ile Cys Ser Leu Tyr Gln Leu Glu Asn Tyr Cys Asn ***              124
```

Fig. 1B

MWPsp-MWPmp9-GSLQPR-Bchain-RGHRP-Linker-PR-Achain-MWPsp*-hPDI*

1 GTCGTTAACAGTGTATTGGCTAGTGCACTCGCACTTACTGTTGCTCCA 48

1 ValValAsnSerValLeuAlaSerAlaLeuAlaLeuThrValAlaPro 16

49 ATGGCTTTCGCAGCAGAAGAAGCAGCAACTACTACAGCTGGGTCCCTG 96

17 MetAlaPheAlaAlaGluGluAlaAlaThrThrThrAlaGlySerLeu 32

97 CAGCCACGTTTTGTGAACCAACACCTGTGCGGCTCACACCTGGTGGAA 144

33 GlnProArgPheValAsnGlnHisLeuCysGlySerHisLeuValGlu 48

145 GCTCTCTACCTAGTGTGCGGGGAAAGAGGCTTCTTCTACACACCCAAG 192

49 AlaLeuTyrLeuValCysGlyGluArgGlyPhePheTyrThrProLys 64

193 ACCCGCGGTCACCGTCCAGAGGCAGAGGACCTGCAGGTGGGGCAGGTG 240

65 ThrArgGlyHisArgProGluAlaGluAspLeuGlnValGlyGlnVal 80

241 GAGCTGGGCGGGGGCCCTGGTGCAGGCAGCCTGCAGCCCTTGGCCCTG 288

81 GluLeuGlyGlyGlyProGlyAlaGlySerLeuGlnProLeuAlaLeu 96

Continued from Fig. 1B

```
289 GAGGGGTCCCTGCAGCCACGTGGCATTGTGGAACAATGCTGTACCAGC   336
 97 GluGlySerLeuGlnProArgGlyIleValGluGlnCysCysThrSer   112

337 ATCTGCTCCCTCTACCAGCTGGAGAACTACTGCAACTAGTATACTAGA   384
113 IleCysSerLeuTyrGlnLeuGluAsnTyrCysAsn***            128

385 GGAGGAGAACACAAGGTTATGAAAAAGGTCGTTAACAGTGTATTGGCT   432
129                MetLysLysValValAsnSerValLeuAla     144

433 AGCGCTCTCGCACTTACTGTTGCTCCAATGGCTTTCGCAGCCCCCGAG   480
145 SerAlaLeuAlaLeuThrValAlaProMetAlaPheAlaAlaProGlu   160

481 GAGGAGGACCACGTCCTGGTGCTGCGGAAAAGCAACTTCGCGGAGGCG   528
161 GluGluAspHisValLeuValLeuArgLysSerAsnPheAlaGluAla   176

529 CTGGCGGCCCACAAGTACCTGCTGGTGGAGTTCTATGCCCCTTGGTGT   576
177 LeuAlaAlaHisLysTyrLeuLeuValGluPheTyrAlaProTrpCys   192
```

Continued from Fig. 1B

```
577 GGCCACTGCAAGGCTCTGGCCCCTGAGTATGCCAAAGCCGCTGGGAAG  624
193 GlyHisCysLysAlaLeuAlaProGluTyrAlaLysAlaAlaGlyLys   208

625 CTGAAGGCAGAAGGTTCCGAGATCAGGTTGGCCAAGGTGGACGCCACG   672
209 LeuLysAlaGluGlySerGluIleArgLeuAlaLysValAspAlaThr   224

673 GAGGAGTCTGACCTGGCCCAGCAGTACGGCGTGCGCGGCTATCCCACC   720
225 GluGluSerAspLeuAlaGlnGlnTyrGlyValArgGlyTyrProThr   240

721 ATCAAGTTCTTCAGGAATGGAGACACGGCTTCCCCCAAGGAATATACA   768
241 IleLysPhePheArgAsnGlyAspThrAlaSerProLysGluTyrThr   256

769 GCTGGCAGAGAGGCTGATGACATCGTGAACTGGCTGAAGAAGCGCACG   816
257 AlaGlyArgGluAlaAspAspIleValAsnTrpLeuLysLysArgThr   272
```

Continued from Fig. 1B

```
 817 GGCCCGGCTGCCACCACCCTGCCTGACGGCGCAGCTGCAGAGTCCTTG       864
 273 GlyProAlaAlaThrThrLeuProAspGlyAlaAlaAlaGluSerLeu       288

865 GTGGAGTCCAGCGAGGTGGCTGTCATCGGCTTCTTCAAGGACGTGGAG       912
 289 ValGluSerSerGluValAlaValIleGlyPhePheLysAspValGlu       304

913 TCGGACTCTGCCAAGCAGTTTTTGCAGGCAGCAGAGGCCATCGATGAC       960
 305 SerAspSerAlaLysGlnPheLeuGlnAlaAlaGluAlaIleAspAsp       320

961 ATACCATTTGGGATCACTTCCAACAGTGACGTGTTCTCCAAATACCAG      1008
 321 IleProPheGlyIleThrSerAsnSerAspValPheSerLysTyrGln       336

1009 CTCGACAAAGATGGGGTTGTCCTCTTTAAGAAGTTTGATGAAGGCCGG      1056
 337 LeuAspLysAspGlyValValLeuPheLysLysPheAspGluGlyArg       352

1057 AACAACTTTGAAGGGGAGGTCACCAAGGAGAACCTGCTGGACTTTATC      1104
 353 AsnAsnPheGluGlyGluValThrLysGluAsnLeuLeuAspPheIle       368
```

Continued from Fig. 1B

```
1105 AAACACAACCAGCTGCCCCTTGTCATCGAGTTCACCGAGCAGACAGCC 1152
 369 LysHisAsnGlnLeuProLeuValIleGluPheThrGluGlnThrAla  384

1153 CCGAAGATTTTTGGAGGTGAAATCAAGACTCACATCCTGCTGTTCTTG 1200
 385 ProLysIlePheGlyGlyGluIleLysThrHisIleLeuLeuPheLeu  400

1201 CCCAAGAGTGTGTCTGACTATGACGGCAAACTGAGCAACTTCAAAACA 1248
 401 ProLysSerValSerAspTyrAspGlyLysLeuSerAsnPheLysThr  416

1249 GCAGCCGAGAGCTTCAAGGGCAAGATCCTGTTCATCTTCATCGACAGC 1296
 417 AlaAlaGluSerPheLysGlyLysIleLeuPheIlePheIleAspSer  432

1297 GACCACACCGACAACCAGCGCATCCTCGAGTTCTTTGGCCTGAAGAAG 1344
 433 AspHisThrAspAsnGlnArgIleLeuGluPhePheGlyLeuLysLys  448

1345 GAAGAGTGCCCGGCCGTGCGCCTCATCACCCTGGAGGAGGAGATGACC 1392
 449 GluGluCysProAlaValArgLeuIleThrLeuGluGluGluMetThr  464
```

Continued from Fig. 1B

```
1393 AAGTACAAGCCCGAATCGGAGGAGCTGACGGCAGAGAGGATCACAGAG  1440
 465 LysTyrLysProGluSerGluGluLeuThrAlaGluArgIleThrGlu   480

1441 TTCTGCCACCGCTTCCTGGAGGGCAAAATCAAGCCCCACCTGATGAGC  1488
 481 PheCysHisArgPheLeuGluGlyLysIleLysProHisLeuMetSer   496

1489 CAGGAGCTGCCGGAGGACTGGGACAAGCAGCCTGTCAAGGTGCTTGTT  1536
 497 GlnGluLeuProGluAspTrpAspLysGlnProValLysValLeuVal   512

1537 GGGAAGAACTTTGAAGACGTGGCTTTTGATGAGAAAAAAAACGTCTTT  1584
 513 GlyLysAsnPheGluAspValAlaPheAspGluLysLysAsnValPhe   528

1585 GTGGAGTTCTATGCCCCATGGTGTGGTCACTGCAAACAGTTGGCTCCC  1632
 529 ValGluPheTyrAlaProTrpCysGlyHisCysLysGlnLeuAlaPro   544

1633 ATTTGGGATAAACTGGGAGAGACGTACAAGGACCATGAGAACATCGTC  1680
 545 IleTrpAspLysLeuGlyGluThrTyrLysAspHisGluAsnIleVal   560
```

Continued from Fig. 1B

```
1681 ATCGCCAAGATGGACTCGACTGCCAACGAGGTGGAGGCCGTCAAAGTT    1728
 561 IleAlaLysMetAspSerThrAlaAsnGluValGluAlaValLysVal     576

1729 CATAGCTTCCCCACACTCAAGTTCTTTCCTGCCAGTGCCGACAGGACG    1776
 577 HisSerPheProThrLeuLysPhePheProAlaSerAlaAspArgThr     592

1777 GTCATTGATTACAACGGGGAACGCACGCTGGATGGTTTTAAGAAATTC    1824
 593 ValIleAspTyrAsnGlyGluArgThrLeuAspGlyPheLysLysPhe     608

1825 CTGGAGAGCGGTGGCCAGGATGGGGCAGGGGATGATGACGATCTCGAG    1872
 609 LeuGluSerGlyGlyGlnAspGlyAlaGlyAspAspAspAspLeuGlu     624

1873 GACCTGGAAGAAGCAGAGGAGCCAGACATGGAGGAAGACGATGATCAG    1920
 625 AspLeuGluGluAlaGluGluProAspMetGluGluAspAspAspGln     640

1921 AAAGCTGTGAAAGATGAACTGTAA                            1944
 641 LysAlaValLysAspGluLeu***                             648
``` pNU-mPINS: X=MWPsp-MWPmp9-GSLQPR-B chain-RGHRP-Linker-PR-A chain pNU-mPINS~hPDI*: X=MWPsp-MWPmp9-GSLQPR-B chain-RGHRP-Linker-PR-A chain-MWPsp*-hPDI*

PROCESS FOR PRODUCING POLYPEPTIDE HAVING DISULFIDE BOND

TECHNICAL FIELD

The present invention relates to DNA which enables co-expression of protein disulfide isomerase and a polypeptide having disulfide bonds, and a process for producing a polypeptide having disulfide bonds, which is obtained through expression of the DNA in bacteria of the genus *Bacillis* and in which correct disulfide bonds are formed.

BACKGROUND ART

Physiologically active substances, such as hormones and enzymes, which play important roles in life activity, are proteins (polypeptides), and the high order structure is important in maintaining the activity. A disulfide bond that is formed between two cysteines is a component forming a high order structure. For example, insulin is secreted from B cells in the islets of Langerhans in the pancreas and is the most important hormone in storing or using sugar, amino acid and fatty acid, and in maintaining homeostasis of blood glucose levels. Insulin is a polypeptide that consists of an A chain comprising 21 amino acids and a B chain comprising 30 amino acids, and has one disulfide bond within the A chain and two disulfide bonds between the A chain and the B chain. When these 3 disulfide bonds are formed inaccurately, insulin will have no activity. Disulfide bonds are thought to be formed by enzymes, such as thioredoxin and protein disulfide isomerase, under an oxidation-reduction environment formed by glutathione and the like in a process where translated proteins are secreted to the endoplasmic reticulum and then transferred to the Golgi complex (Hwang, C. et al., Science 257: 1496–1502, (1992)., Gething, M. & Sambrook, J., Nature 355: 33–45, (1992), Bardwell, J. C. A. & Beckwith, J., Cell 74: 769–771, (1993)). It has been shown that these enzymes act to form disulfide bonds in in vitro experiments where the disulfide bond formation of proteins denatured to have no disulfide bond is enhanced when they are placed under reduction conditions and under the presence of the enzymes (Lyles, M. M. & Gilbert, H. F., Biochemistry 30: 613–619, (1991)., Lyles, M. M. & Gilbert, H. F., Biochemistry 30: 619–625, (1991)., Pigiet, V. F. & Schuster, B. J. Proc. Natl. Acad. Sci. USA 83:7643–7647, (1986)). Further, protein disulfide isomerase is known to have an effect of rearranging incorrect disulfide bonds into correct disulfide bonds (Weissman, J. S. & Kim, P. S, Nature 365:185–188, (1993)., Laboissiere, M. C. A. et al., J. Biol. Chem. 270: 28006–28009, (1995)).

Some physiologically active polypeptides that are present only in trace amounts in vivo, such as insulin, glucagon, interferon, calcitonin and growth hormone, are now being produced using established gene recombination techniques in large amounts as gene-recombinant proteins in prokaryotes and eukaryotes. In particular, an expression system in prokaryotes is widely used because of the large amount produced and the low production costs. However, among expression systems of prokaryotes, particularly a system in which proteins are expressed as inclusions within the cells of *Escherichia coli* has the advantage of a large amount of expression, but such a system cannot provide an environment for disulfide bond formation. Hence, proteins having disulfide bonds expressed in this expression system must be denatured once after isolation and purification, and then an environment for disulfide bond formation must be established. These steps are complex and may increase the cost.

In contrast, a system in which proteins are expressed in the periplasm of *Escherichia coli* is an environment which enables disulfide bond formation therewithin, but the expression amount is limited. Moreover, a yeast expression system enables disulfide bond formation within the cells before secretion, but its expression amount is low.

A recently developed expression system of gene-recombinant protein using *Bacillus brevis* (*Bacillus brevis*; referred to as bacteria of the genus *Brevibacillus* according to a new classification) has received attention as a mass production system of gene-recombinant proteins with disulfide bonds, because polypeptides having disulfide bonds (human epidermal growth factor and the like) in an active state, that is, having accurately formed disulfide bonds are secreted and expressed in large amounts in media (Japanese Patent No. 2082727, Japanese Patent Application Laying-Open (Kokai) No. 62-201583, Konishi, H. et al., Appl. Microbiol. Biotechnol., 34:297–302 (1990), Shigezo UDAKA, Journal of Japan Society for Bioscience, Biotechnology and Agrochemistry 61, 669–676 (1987), Sagiya, Y. et al., Appl. Microbiol. Biotechnol., 42:358–363 (1994), Yamagata, H. et al., Proc. Natl. Acad. Sci. USA 86: 3589–3593 (1989)). However, it has recently been found that the rate of correct disulfide bond formation is not 100% in this expression system (Miyauchi, A. et al., J. Indust. Microbiol. Biotech., 21: 208–214, (1998)). The rate of correct disulfide bond formation seems to differ depending on the types of polypeptides. For example, the formation rate of a human epidermal growth factor is 80%.

To date, it is known that protein disulfide isomerase is involved in the intracellular formation of correct disulfide bonds of a protein. Particularly regarding yeast, there has been a report that co-expression of the gene of protein disulfide isomerase involved in disulfide bond formation and the gene of a protein having disulfide bonds has enabled production of proteins having correct disulfide bonds (Japanese Patent Application Laying-Open (Kokai) Nos. 6-38771 and 7-508881). Generally, in yeast, the eukaryote, disulfide bonds are formed while the protein is transferred from intracellular endoplasmic reticulum to the Golgi complex, and then secreted extracellularly after completion of the high order structure of the protein. As an example in bacteria, there has been a report that a target protein gene has been ligated to the gene of protein disulfide isomerase of molds and expressed in an expression system of bacteria of the genus *Bacillus*. In this example, protein disulfide isomerase is expressed as a fusion protein with the protein (Japanese Patent Application Laying-Open (Kokai) No. 11-75879).

An object of the present invention is to increase efficiency of the production of polypeptides with correct disulfide bonds in a bacterial expression system for genes encoding proteins where it is difficult or impossible for such bonds to form. This is done by allowing co-expression of a gene encoding a polypeptide having disulfide bonds and a gene encoding protein disulfide isomerase, so as to establish an environment wherein the polypeptide and protein disulfide isomerase co-exist. In this case, it is required to surmount problems of how an expression/secretion system should be established to allow co-expression of the gene encoding a polypeptide and the gene encoding protein disulfide isomerase within bacterial cells, to allow extracellular secretion of both the generated proteins, and to allow extracellular formation of correct disulfide bonds in the polypeptide.

DISCLOSURE OF THE INVENTION

To achieve the above object, we have cloned and ligated the gene of protein disulfide isomerase to the gene of a polypeptide having disulfide bonds, thereby designing and constructing an expression/secretion system in bacteria in which both gene products are simultaneously secreted in medium. Hence, we were able to establish an environment in bacteria allowing co-existence of protein disulfide isomerase and a polypeptide having disulfide bonds, and thus increased correct disulfide bond formation in polypeptides having disulfide bonds.

Specifically, the present invention is summarized as follows.

In a first aspect of the present invention, there is provided a DNA which enables co-expression of a protein disulfide isomerase and a polypeptide having disulfide bonds, comprising one or two identical or different promoters required for gene expression (Promoter), two identical or different Shine-Dalgarno sequences (SD), two identical or different sequences encoding signal peptides of cell wall proteins (CWP) of a bacterium of the genus *Bacillus* (CWPsp), a gene encoding a polypeptide having disulfide bonds (Polypeptide), and a gene encoding protein disulfide isomerase (PDI) that are ligated to each other as represented by the following formula:

5'-Promoter-SD-CWPsp-X$_1$-(Promoter)n-SD-CWPsp-X$_2$-3', wherein X$_1$=Polypeptide and X$_2$=PDI, or X$_1$=PD$_1$ and X$_2$=Polypeptide, and n=0 or 1.

In an embodiment of the present invention, the promoter is derived from bacteria of the genus *Bacillus*, for example, it is derived from CWP (for example, MWP (Middle-Wall Protein)) of bacteria of the genus *Bacillus*.

In another embodiment of the present invention, protein disulfide isomerase is derived from a human.

In still another embodiment of the present invention, the polypeptide having disulfide bonds is a fusion protein containing a human insulin and is represented by, for example, the following formula:

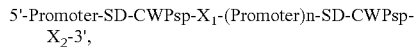

MWPmp9-GSLQPR-B chain-RGHRP-Linker-PR-A chain, wherein MWPmp9 represents 9 amino acids from the N terminus of MWP mature protein; GSLQPR, RGHRP and PR respectively represents an amino acid sequence shown by one-letter codes; A chain and B chain respectively represent the A chain and B chain of human insulin; and Linker represents a linker consisting of any amino acid.

In a specific example of the present invention, a part of a modified insulin C peptide is used as a linker However, examples of linkers are not specifically limited as long as they are capable of linking two domains together without affecting the functional domain of the protein. For example, the appropriate number of Ala, Gly, Pro, Ser and Val may be linked in appropriate combinations.

In another aspect of the present invention, there is provided a vector comprising a DNA as defined above.

In still another aspect of the present invention, there is provided a bacterium of the genus *Bacillus* which is transformed with the above vector. In an embodiment of the present invention, the bacterium of the genus *Bacillus* is *Bacillus brevis*.

In another aspect of the present invention, there is provided a process for producing a polypeptide having disulfide bonds, which comprises the steps of:
 introducing the above vector into a bacterium of the genus *Bacillus*;
 culturing the obtained transformed bacterium in a medium;
 co-expressing a protein disulfide isomerase and the polypeptides having one or more disulfide bonds, thereby secreting together extracellularly; and
 collecting the polypeptide having correct disulfide bonds formed by the action of the protein disulfide isomerase.

In an embodiment of the present invention, the above process further comprises the steps of:
 generating a polypeptide having correct disulfide bonds as a fusion protein; and
 treating the obtained fusion protein with protease to obtain the polypeptide.

In another embodiment of the present invention, the polypeptide is a human insulin.

This specification includes part or all of the contents as disclosed in the specification and/or drawings of Japanese Patent Application No. 2000-70753, which is a priority document of the present application.

BRIEF DESCRIPTION OF DRAWINGS

FIG. 1 shows amino acid sequences of fusion proteins MWPsp-MWPmp9-GSLQPR-B chain-RGHRP-Linker-PR-A chain (FIG. 1A-SEQ ID NOS:24 and 25) and MWPsp-MWPmp9-GSLQPR-B chain-RGHRP-Linker-PR-A chain-MWPsp*-hPDI* (FIG. 1B-SEQ ID NOS:24, 25, and 26) and nucleotide sequences encoding the amino acid sequences.

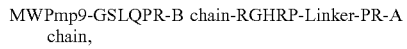

Figure 6:
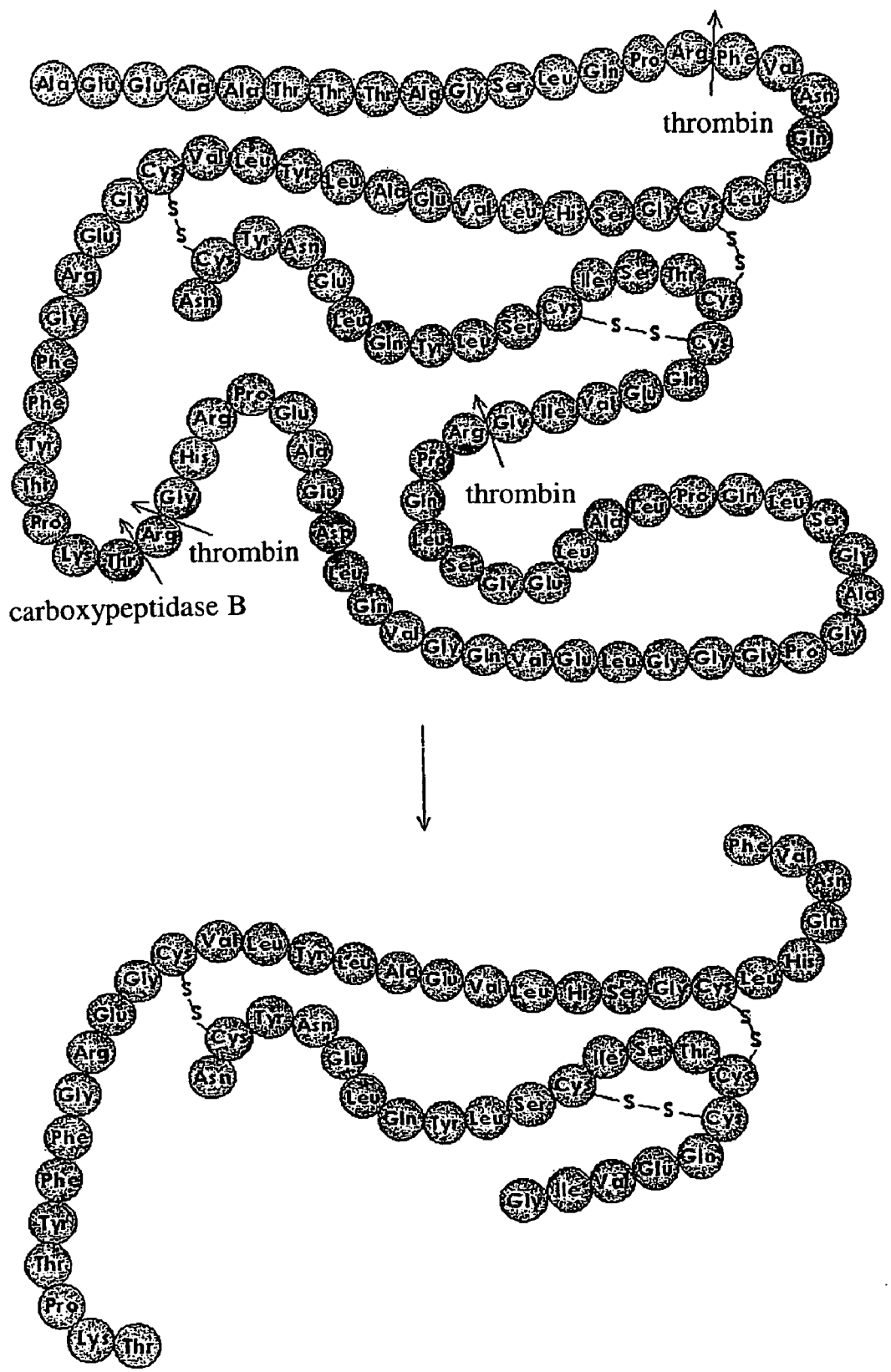

FIG. 6 is a schematic diagram of conversion from a fusion protein MWPmp9-GSLQPR-B chain-RGHRP-Linker-PR-A chain to insulin.

Figure 7:
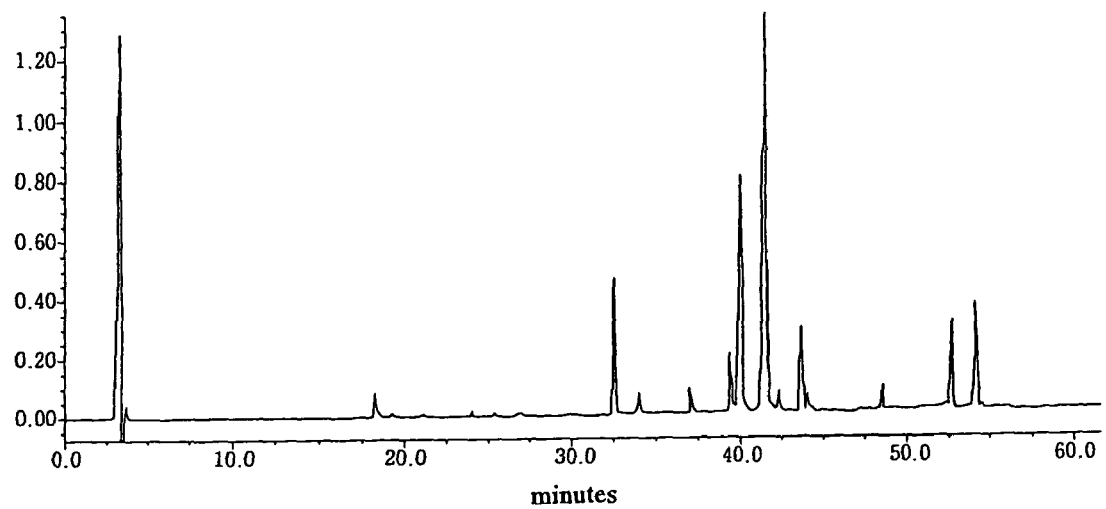
Figure 7:
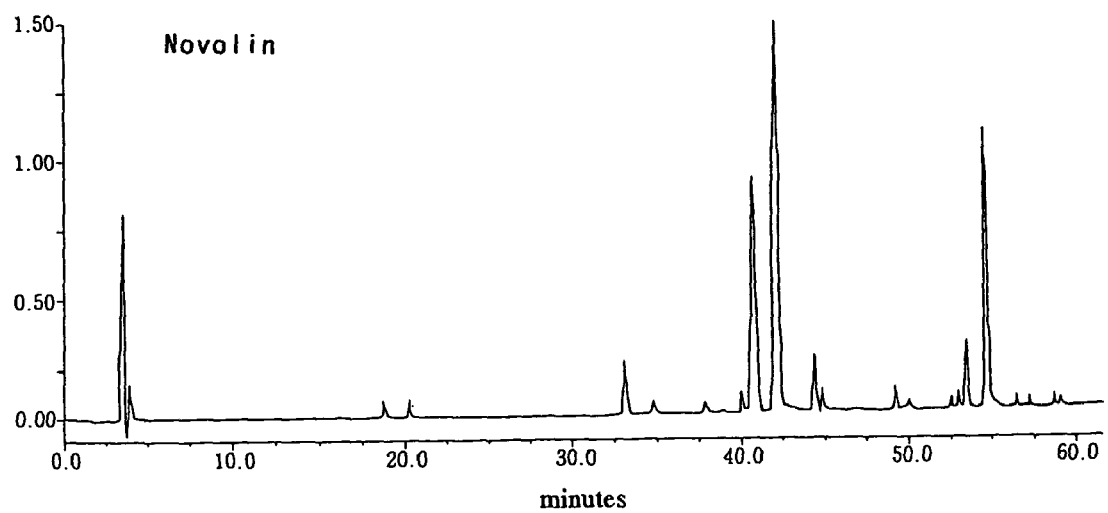

FIG. 7 shows a comparison between peptide mappings of the insulin of the present invention and a commercially available insulin (Novolin).

DETAILED DESCRIPTION OF THE INVENTION

The present invention makes it possible to obtain increased efficiency of the production of polypeptides that have undergone correct disulfide bond formation by allowing protein disulfide isomerase and a polypeptide having disulfide bonds to co-exist in an environment in which no disulfide bond can be formed or where efficiency of disulfide bond formation is low.

Examples of promoters of bacteria of the genus *Bacillus* include those adjustable, and capable of expressing a gene ligated 3' downstream, such as Spac promoters, promoters derived from φ 105 phage, and promoters derived from a structural gene of a host including amilase and protease (Molecular Biological Methods for *Bacillus*, Harwood, C. R. & Cutting, S. M. eds., pp202–203, 1990).

According to the embodiment of the present invention, an appropriate promoter is CWP protein of bacteria of the genus *Bacillus*. Examples of CWP protein include, but are not limited to, MWP protein (J. Bacteriol., 169:1239–1245, 1989) derived from *Bacillus brevis* strain 47 (FERM P-7224: Japanese Patent Application Laying-Open (Kokai) No. 60-58074, Japanese Patent Application Laying-Open (Kokai) No. 62-201589) and HWP protein (J. Bacteriol., 172: 1312–1320, 1990) derived from *Brevibacillus choshinensis*, HPD31 (FERM BP-1087: Japanese Patent Application Laying-Open (Kokai) No. 4-278091). Further, in the present invention, a sequence which encodes a signal peptide of the CWP protein illustrated herein can be used as CWPsp in the above formula.

Protein disulfide isomerase is present generally in organisms having polypeptides which require disulfide bonds, such as yeast, molds and mammals. Any type of protein disulfide isomerase can be used in the present invention, as far as it is an enzyme involved in correct disulfide bond formation of a polypeptide. For example, protein disulfide isomerase may be Dsb A of *Escherichia coli* (Bardwell, J. C. A. et al., Cell, 67:582–589 (1991), Kamitani, S. et al., EMBO J., 11:57–62 (1992)), which is involved in disulfide bond formation of a protein and is thought to relate to protein disulfide isomerase. According to the embodiment of the present invention, an appropriate protein disulfide isomerase is derived from a human.

Examples of a polypeptide having disulfide bonds include an insulin, an epidermal growth factor (EGF), a growth hormone and albumin. For example, a human insulin contains one disulfide bond within the A chain (Cys at position 6 and Cys at position 11 from the N terminus) and two disulfide bonds between the A chain and the B chain (Cys at position 7 from the N terminus of the A chain and Cys at position 7 from the N terminus of the B chain, and Cys at position 20 from the N terminus of the A chain and Cys at position 19 from the N terminus of the B chain). What is common among polypeptides having disulfide bonds is that an correct disulfide bond is essential for the function of the polypeptide. According to the embodiment of the present invention, a polypeptide having disulfide bonds is a fusion protein containing a human proinsulin, MWPmp9-GSLQPR-B chain-RGHRP-Linker-PR-A chain. This fusion protein is highly expressed in *Bacillus brevis*, and the disulfide bonds are accurately and efficiently generated in co-existence with protein disulfide isomerase. When the thus obtained fusion protein is treated with an appropriate protease (for example, thrombin and carboxypeptidase), insulin having physiological activity can be obtained. Insulin is a pharmaceutical preparation essential for the therapy of diabetes. Examples of protease include factor Xa, enterokinase, V8 protease and TEV protease. However in this case, it is necessary to introduce a cleavage site specific to each protease into a fusion protein so as to specifically free the targetted mature protein.

With a method to allow co-expression of protein disulfide isomerase (PDI) and a polypeptide having disulfide bonds, genes encoding each protein are ligated to the 3' downstream of the above promoter so that they can be expressed polycistronically, that is, in the form of Promoter-SD-CWPsp-Polypeptide-SD-CWPsp-PDI. In such a case, it may also be Promoter-SD-CWPsp-PDI-SD-CWPsp-Polypeptide. In the present specification, SD sequence (Shine-Dalgarno sequence) is required to initiate translation of a protein at a site where mRNA binds to a ribosome, and it is preferably derived from bacteria of the genus *Bacillus*. Another method involves the step of ligating a gene that encodes protein disulfide isomerase to the 3' downstream of the promoter and then ligating a gene that encodes a polypeptide having disulfide bonds to the 3' downstream of the promoter, so that the genes are ligated in a series. That is, the series takes the form of Promoter-SD-CWPsp-Polypeptide-Promoter-SD-CWPsp-PDI. In such a case, it may also be Promoter-SD-CWPsp-PDI-Promoter-SD-CWPsp-Polypeptide.

The DNA of the present invention can be prepared using a combination of techniques known in the art. For example, a target DNA can be prepared by a combination of preparing each constitutive DNA sequence by a chemical synthesis method or a cloning method, ligating in sequence these constituents using ligase, and using a PCR amplification method. Specifically, the details of preparation can be understood by referring to the examples. General techniques that can be used herein are described individually in Maniatis, T. el al., Molecular Cloning 2nd ed., A Laboratory Manual, Cold Spring Harbor Laboratory (1989), Innis, M. A. et al., PCR Protocols, A guide to methods and applications, Academic Press (1990) and the like.

DNAs encoding human proinsulin which contains the B chain of insulin, C peptide and an A chain can be obtained from a commercially available mRNA of human pancreas using a commercially available cDNA 1 st-strand synthesis kit or the like. Further, if short-strand DNAs that are used as primers can be synthesized based on known DNA sequences using a commercially available DNA synthesizer, desired DNA fragments including B chain, C peptide, A chain and the like can be amplified by a general polymerase chain reaction (PCR). DNA encoding human protein disulfide isomerase can also be obtained similarly from a commercially available mRNA of human pancreas by a PCR amplification method. In the PCR amplification method, a cycle consisting of denaturation of DNA, annealing with primers and an elongation reaction is repeated 20 cycles or more.

Figure 2:
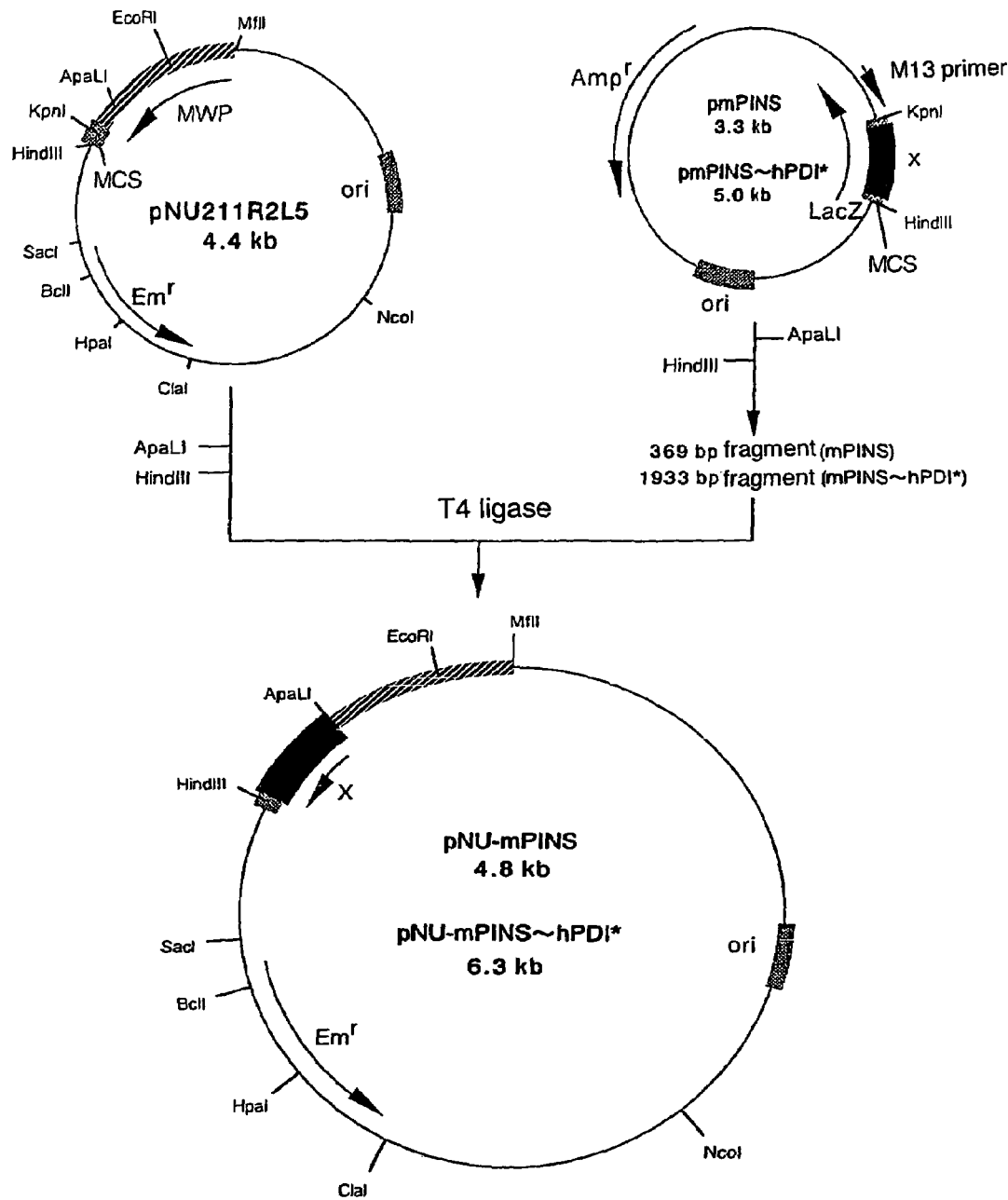
FIG. 2 is a schematic view showing the steps for incorporating fusion DNAs obtained in Examples 1 and 2 into an expression vector (pNU211R2L5) of *Bacillus brevis*.

According to the present invention, a vector comprising the above DNA of the present invention is further provided. Vectors that can be used herein should have at least the following properties of: having an appropriate insertion site, that is, a restriction enzyme site, to which the DNA of the present invention can be incorporated; enabling expression of the DNA within a host cell; and being capable of autonomously replicating within the host cell. The vector may contain a replication origin and a terminator sequence. In addition, a selection marker, such as a drug resistance gene, a gene complementing auxotrophy or the like may be included. Preferably, the vector of the present invention is a plasmid which is capable of replicating in bacteria of the genus *Bacillus*. Examples of such vectors that can be used herein include, but are not limited to, pNU200, pHY500 (Proc. Natl. Acad. Sci. USA, 86:3589–3593, 1989), pHY4831 (J. Bacteriol., 169:1239–1245, 1987), pNU100 (Appl. Microbiol. Biotechnol., 30:75–80, 1989), pNU211 (J. Biochem., 112:488–491, 1992), pNU211R2L5 (Japanese Patent Application Laying-Open (Kokai) No. 7-170984), pHY700 (Japanese Patent Application Laying-Open (Kokai) No. 4-278091), pHT210 (Japanese Patent Application Laying-Open (Kokai) No. 6-133782), pHT110R2L5 (Appl. Microbiol. Biotechnol., 42:358–363, 1994). According to specific examples of the present invention, an expression vector, pNU-mPINS-hPDI* can be prepared by a construction method as shown in FIG. 2.

According to the present invention, bacteria of the genus *Bacillus* transformed with the above-defined vector are provided. Examples of bacteria of the genus *Bacillus* as hosts include, but are not limited to, *Bacillus brevis* strain 47 (FERM P-7224: Japanese Patent Application Laying-Open (Kokai) No.60-58074, Japanese Patent Application Laying-Open (Kokai) No. 62-201589), 47K (Japanese Patent Application Laying-Open (Kokai) No.2-257876), from *Brevibacillus choshinensis* 31 OK (Japanese Patent Application Laying-Open (Kokai) No.6-296485 and HPD31 (FERM BP-1087; Japanese Patent Application Laying-Open (Kokai) No.4-278091). Recombinant bacteria obtained by transferring the expression vector, pNU-mPINS-hPDI*, into *Bacillus brevis* strain 47 5Q was deposited under the terms of the Budapest Treaty on Feb. 24, 2000 at the National Institute of Bioscience and Human, Agency of Industrial Science and technology, Ministry of economy, trade and industry, Japan (1-3, Higashi 1-chome, Tsukuba-shi, Ibaraki, Japan) (the present name: the International Patent Organism Depository (IPOD), National Institute of Advanced Industrial Science and Technology, Japan (1-1, Higashi 1-chome, Tsukuba-shi, Ibaraki, Japan)) under the accession No. FERM BP-7055.

Expression vectors obtained as described above are transferred into competent bacteria of the genus *Bacillus* by a method, such as electroporation (Methods in Enzymol., 217: 23–33, 1993). The bacteria are cultured in appropriate media under conditions that enable expression, and then polypeptides having disulfide bonds and protein disulfide isomerase are secreted extracellularly, so that a state wherein the two can co-exist in the media can be provided. Thus, protein disulfide isomerase can increase the efficiency of accurate formation of disulfide bonds of polypeptides having disulfide bonds. When disulfide bonds are accurately formed in a polypeptide, the polypeptide will have physiological activity. Further, industrial applications are expected for the polypeptide isolated and purified from media by a combined use of methods including gel filtration chromatography, ion exchange chromatography, affinity chromatography, hydrophobic interaction chromatography, electrophoresis and isoelectric electrophoresis. Further, a fusion protein containing proinsulin that is used as a polypeptide having disulfide bonds in the present invention is converted to insulin by treating with thrombin and carboxypeptidase B. Hence, the production amount of insulin having correct disulfide bonds, that is, insulin having physiological activity as a result of co-existence with protein disulfide isomerase, can be increased.

Therefore, according to the present invention, there can be provided a method for increasing the efficiency of correct disulfide bond formation for gene-recombinant polypeptides having disulfide bonds by culturing bacteria of the genus *Bacillus* transformed with the above expression vector in media, and providing a system wherein protein disulfide isomerase and polypeptides having disulfide bonds can co-exist extracellularly.

EXAMPLES

The present invention will be further described in the following examples. The examples are not intended to limit the scope of the invention.

A method employed in the following Examples to prepare DNA which encodes a fusion protein involves ligating DNA fragments amplified by a PCR reaction (polymerase chain reaction) by a ligation reaction using DNA ligase. MWPsp represents a signal peptide of MWP protein, and MWPmp9 represents 9 amino acids from the N terminus of MWP mature protein. Regarding MWPmp9-GSLQPR-B chain-RGHRP-Linker-PR-A chain, the letters in GSLQPR, RGHRP and PR are commonly used one-letter symbols for amino acids. B chain and A chain represent respectively the B chain and A chain of insulin. In addition, Linker is a part of C peptide of insulin.

Example 1

Construction of Vector (pmPINS) Having MWPsp-MWPmp9-GSLQPR-B Chain-RGHRP-Linker-PR-A Chain Fusion DNA Incorporated Therein (1) Preparation of DNA Fragment, MWPsp-MWPmp9 a. Template DNA

Genome DNA (840 ng) was extracted from *Bacillus brevis* (strain 47-5Q) by a known method (Molecular Cloning 2nd ed., A Laboratory Manual, Cold Spring Harbor Laboratory (1989)).

b. Primer

Forward primer: 5'-ACACGCGCTTGCAGGATTCG-3' (SEQ ID NO: 1)

Reverse primer: 5'-AGCTGTAGTAGTTGCTGC-3' (SEQ ID NO: 2)

Primers were synthesized by organic chemical synthesis based on the nucleotide sequence of MWP protein determined by Yamagata, H. et al. (J. Bacteriol., 169, 1239–1245, 1987) and Tsuboi, A. et al. (J. Bacteriol., 170, 935–945, 1988). They were added at a final concentration of 0.1 µmol/L.

c. Taq DNA Polymerase

5 U of a commercially available product (GIBCO BRL) was added.

d. Others

Tris-HCl (final concentration of 20 mmol/L, pH 8), $MgCl_2$ (final concentration of 2.5 mmol/L), dNTPs (dATP, dGTP, dCTP and dTTP each at a final concentration of 50 µmol/L) were added.

100 µL of each reaction solution of a to d was put into 0.5 mL tubes, and then PCR reaction was performed by a known method (a reaction cycle was repeated 30 times, each cycle consisting of denaturation temperature of 94° C. for 1 min, annealing temperature of 55° C. for 1 min and DNA strand elongation temperature of 72° C. for 1 min) (Innis, M. A. et al., PCR Protocols, A guide to methods and applications, Academic Press, (1990)). After PCR reaction, the reaction solutions were concentrated with phenol, applied to 0.8% agarose gel, and then subjected to electrophoresis under normal conditions, thereby collecting a PCR product, that is, a DNA fragment, MWPsp-MWPmp9, from the agarose gel with ultra-free C3H (Millipore). The collected PCR product was extracted with phenol, subjected to ethanol precipitation, dried in vacuum, and then dissolved in an appropriate amount of distilled water. Blunt end reaction was performed using a DNA blunting kit (TAKARA SHUZO CO., LTD.) by a method according to the instructions.

(2) Preparation of DNA Fragment, Proinsulin

A blunt-ended DNA fragment, proinsulin, was obtained by procedures similar to (1) except for the following procedures.

As a template DNA, 10 ng of a plasmid vector having human preproinsulin DNA incorporated therein was used. The plasmid vector having the human preproinsulin DNA incorporated therein was obtained as follows. Human pancreas cDNA was synthesized using a $1^{st}$ strand cDNA synthesis kit (Pharmacia) from a commercially available mRNA of human pancreas (CLONTECH) according to the instructions. Using the cDNA as a template and a forward primer 5'-ATGGC-CCTGTGGATGCGCC-3' (SEQ ID NO: 3) and a reverse primer 5'-CTAGTTGCAGTAGTTCTCC-3' (SEQ ID NO: 4) synthesized based on the nucleotide sequence of a human preproinsulin gene that had been determined by Bell, G. I. et al (Nature, 282, 525–527, (1979)), PCR reaction was performed (conditions: a reaction cycle was repeated 35 times, each cycle consisting of 94° C. for 1 min, 60° C. for 1 min and 72° C. for 1 min). The resulting PCR product, that is, human preproinsulin DNA, was cloned into a pGEM-T vector (Promega).

As primers, a forward primer 5'-TTTGTGAACCAA-CACCTG-3' (SEQ ID NO: 5) and a reverse primer 5'-CTAGTTGCAGTAGTTCTCC-3' (SEQ ID NO: 6) were used.

PCR reaction conditions employed herein comprise a reaction cycle repeated 25 times, each cycle consisting of a denaturation temperature of 94° C. for 1 min, an annealing temperature of 47° C. for 1 min and a DNA strand elongation temperature of 72° C. for 30 sec.

(3) Preparation of DNA Fragment, GSLQPR-B Chain-R

A blunt-ended DNA fragment GSLQPR-B chain-R was obtained by procedures similar to (1) except for the following procedures. Further, phosphorylation (T4 polynucleotide kinase (NIPPON GENE) was used according to the instructions) was performed to obtain a phosphorylated DNA fragment GSLQPR-B chain-R.

As a template DNA, the PCR product of proinsulin (10 ng) obtained in (2) was used.

As primers, a forward primer 5'-GGTTCCTTGCAAC-CTCGTTTTGTGAACCAACACCTG-3' (SEQ ID NO: 7) and a reverse primer 5'-GCGGGTCTTGGGT-GTGTA-3' (SEQ ID NO: 8) were used.

PCR reaction conditions employed herein comprise a reaction cycle repeated 25 times, each cycle consisting of a denaturation temperature of 94° C. for 1 min, an annealing temperature of 47° C. for 1 min and a DNA strand elongation temperature of 72° C. for 30 sec.

(4) Preparation of DNA Fragment, Linker

A blunt-ended DNA fragment, Linker, was obtained by procedures similar to (1) except for the following procedures.

As a template DNA, 10 ng of the PCR product of proinsulin obtained in (2) was used.

As primers, a forward primer 5'-GAGGCAGAGGACCT-GCAG-3' (SEQ ID NO: 9) and a reverse primer 5'-CT-GCAGGGACCCCTCCAG-3' (SEQ ID NO: 10) were used.

PCR reaction conditions employed herein comprise a reaction cycle repeated 25 times, each cycle consisting of a denaturation temperature 94° C. for 1 min, an annealing temperature of 55° C. for 1 min and a DNA strand elongation temperature of 72° C. for 30 sec.

(5) Preparation of DNA Fragment, GHRP-Linker

A blunt-ended DNA fragment GHRP-Linker was obtained by procedures similar to (4) except for the following procedures. Further, phosphorylation (T4 polynucleotide kinase (NIPPON GENE) was used according to the instructions) was performed to obtain a phosphorylated DNA fragment GHRP-Linker.

As a template DNA, 10 ng of the PCR product of the DNA fragment, Linker, obtained in (4) was used.

As a forward primer, 5'-GGTCACCGTCCAGAGGCA-GAGGACCTGCAGGTGGGG-3' (SEQ ID NO: 11) was used.

PCR reaction conditions employed herein comprise a reaction cycle repeated 25 times, each cycle consisting of a denaturation temperature of 94° C. for 1 min, an annealing temperature of 55° C. for 1 min and a DNA strand elongation temperature of 72° C. for 30 sec.

(6) Preparation of DNA Fragment, A Chain

A blunt-ended DNA fragment A chain was obtained by procedures similar to (1) except for the following procedures.

As a template DNA, 10 ng of the PCR product of proinsulin obtained in (2) was used.

As primers, a forward primer 5'-GGCATTGTGGAA-CAATGCTGT-3' (SEQ ID NO: 12) and a reverse primer 5'-CTAGTTGCAGTAGTTCTCCAGCTG-GTA-3' (SEQ ID NO: 13) were used.

PCR reaction conditions employed herein comprise a reaction cycle repeated 25 times, each cycle consisting of a denaturation temperature of 94° C. for 1 min, an annealing temperature of 55° C. for 1 min and a DNA strand elongation temperature of 72° C. for 30 sec.

(7) Preparation of DNA Fragment, PR-A Chain

A blunt-ended DNA fragment PR-A chain was obtained by procedures similar to (6) except for the following procedures. Further, phosphorylation (T4 polynucleotide kinase (NIPPON GENE) was used according to the instructions) was performed to obtain a phosphorylated DNA fragment PR-A chain.

As a template DNA, 10 ng of the PCR product of the DNA fragment A chain, obtained in (6) was used.

As a forward primer, 5'-CCACGTGGCATTGTGGAA-CAATGCTGT-3' (SEQ ID NO: 14) was used.

PCR reaction conditions employed herein comprise a reaction cycle repeated 25 times, each cycle consisting of a denaturation temperature of 94° C. for 1 min, an annealing temperature of 55° C. for 1 min and a DNA strand elongation temperature of 72° C. for 30 sec.

(8) Preparation of Fusion DNA, MWPsp-MWPmp9-GSLQPR-B Chain-R

A blunt-ended fusion DNA, MWPsp-MWPmp9-GSLQPR-B chain-R was obtained by procedures similar to (1) except for the following procedures.

A template DNA used herein was prepared by mixing an appropriate amount of the DNA fragment MWPsp-MWPmp9 obtained in (1) and an appropriate amount of the DNA fragment GSLQPR-B chain-R obtained in (3), and then performing reaction using a DNA ligation kit (TAKARA SHUZO CO., LTD.) at 16° C. for 30 min.

As a reverse primer, 5'-GCGGGTCTTGGGTGTGTA-3' (SEQ ID NO: 8) was used.

PCR reaction conditions employed herein comprise a reaction cycle repeated 25 times, each cycle consisting of a denaturation temperature of 94° C. for 1 min, an annealing temperature of 47° C. for 1 min and a DNA strand elongation temperature of 72° C. for 30 sec.

Subsequently, the PCR product was phosphorylated using T4 polynucleotide kinase (NIPPON GENE) according to the instructions. The phosphorylated PCR product was cut with a restriction enzyme Hinc II using a DNA ligation kit (TAKARA SHUZO CO., LTD.), and then incorporated into a vector (STRATAGENE, Blue Script SK-). According to a known method (Molecular Cloning 2nd ed., A Laboratory Manual, Cold Spring Harbor Laboratory (1989)), *Escherichia coli* DH5α was transformed, and then a plasmid DNA, the vector, was purified from the transformant. Using a forward primer (M13 forward primer) or a reverse primer (M13 reverse primer) for determining the nucleotide sequence of a vector, the nucleotide sequence was determined, thereby confirming that a fusion DNA MWPsp-MWPmp9-GSLQPR-B chain-R was prepared. Next, using a vector having MWPsp-MWPmp9-GSLQPR-B chain-R incorporated therein as a template DNA, a forward primer 5'-ACACGCGCTTGCAGGATTCG-3' (SEQ ID NO: 1) and a reverse primer 5'-GCGGGTCTTGGGTGTGTA-3' (SEQ ID NO: 8), a second PCR reaction was performed by a method similar to the above method, thereby obtaining a blunt-ended fusion DNA, MWPsp-MWPmp9-GSLQPR-B chain-R.

(9) Preparation of Fusion DNA, MWPsp-MWPmp9-GSLQPR-B Chain-RGHRP-Linker

A blunt-ended fusion DNA, MWPsp-MWPmp9-GSLQPR-B chain-RGHRP-Linker, was obtained by procedures similar to (8) except for the following procedures.

A template DNA for a first PCR reaction employed herein was prepared by mixing an appropriate amount of the fusion DNA, MWPsp-MWPmp9-GSLQPR-B chain-R, obtained in (8) and an appropriate amount of the DNA fragment, GHRP-Linker, obtained in (5), and performing reaction using a DNA ligation kit (TAKARA SHUZO CO., LTD) at 16° C. for 30 min.

As a reverse primer, 5'-CTGCAGGGACCCCTCCAG-3' (SEQ ID NO: 10) was used.

(10) Preparation of Vector Having Fusion DNA, MWPsp-MWPmp9-GSLQPR-B Chain-RGHRP-Linker-PR-A Chain, Incorporated Therein A vector (pmPINS) having a fusion DNA, MWPsp-MWPmp9-GSLQPR-B chain-RGHRP-Linker-PR-A chain, incorporated therein was obtained by procedures similar to (8) except for the following procedures.

A template DNA for a first PCR reaction employed herein was prepared by mixing an appropriate amount of the fusion DNA, MWPsp-MWPmp9-GSLQPR-B chain-RGHRP-Linker, obtained in (9) and an appropriate amount of the DNA fragment, PR-A chain, obtained in (7), and performing reaction using a DNA ligation kit (TAKARA SHUZO CO., LTD) at 16° C. for 30 min.

As a reverse primer for a first PCR reaction, 5'-CTAGTTGCAGTAGTTCTCCAGCTGGTA-3' (SEQ ID NO: 13) was used.

PCR reaction conditions employed herein comprise a reaction cycle repeated 25 times, each cycle consisting of a denaturation temperature of 94° C. for 1 min, an annealing temperature of 50° C. for 1 min and a DNA strand elongation temperature of 72° C. for 1 min.

Example 2

Construction of Vector (pmPINS~hPDI*) Having Fusion DNA, MWPsp-MWPmp9-GSLQPR-B Chain-RGHRP-Linker-PR-A Chain-MWPsp*-hPDI*, Incorporated Therein (1) Preparation of DNA Fragment, MWPsp-MWPmp9-GSLQPR-B Chain-RGHRP-Linker-PR-A Chain A blunt-ended DNA fragment, MWPsp-MWPmp9-GSLQPR-B chain-RGHRP-Linker-PR-A chain was Obtained by Procedures Similar to (1) of Example 1 except for the following procedures.

As a template DNA, 10 ng of a plasmid vector having the DNA fragment, MWPsp-MWPmp9-GSLQPR-B chain-RGHRP-Linker-PR-A chain, incorporated therein was used.

As a reverse primer, 5'-CTAGTTGCAGTAGTTCTCCAGCTGGTA-3' (SEQ ID NO: 13) was used.

PCR reaction conditions employed herein comprise a reaction cycle repeated 25 times, each cycle consisting of a denaturation temperature of 94° C. for 1 min, an annealing temperature of 53° C. for 1 min and a DNA strand elongation temperature of 72° C. for 30 sec.

(2) Preparation of DNA Fragment, Human Protein Disulfide Isomerase (hPDI)

A blunt-ended and phosphorylated DNA fragment, hPDI, was obtained by procedures similar to Example 1 (1) except for the following procedures.

As a template DNA, a plasmid vector (10 ng) having hPDI DNA incorporated therein was used. The plasmid vector having hPDI DNA incorporated therein was obtained as follows. Human pancreas cDNA was synthesized using a 1$^{st}$ strand cDNA synthesis kit (Pharmacia) from a commercially available mRNA of human pancreas (CLONTECH) according to the instructions. Using the cDNA as a template and a forward primer 5'-GCCCCCGAGGAGGAGGACCACGTCCTG-3' (SEQ ID NO: 15) and a reverse primer 5'-TTACAGTTCATCTTTCACAGCTTTCTG-3' (SEQ ID NO: 16) synthesized based on the nucleotide sequence of a human protein disulfide isomerase gene that had been determined by Pihlajaniemi, T. et al., (The EMBO Journal 6:643–649, 1987), PCR reaction was performed (conditions: 35 repeated cycles, each cycle consisting of 94° C. for 1 min, 60° C. for 1 min and 72° C. for 1 min). The resulting PCR product, that is, DNA was cloned into a pGEM-T vector (Promega).

As primers, a forward primer 5'-GCCCCCGAGGAGGAGGACCACGTCCTG-3' (SEQ ID NO: 15) and a reverse primer 5'-TTACAGTTCATCTTTCACAGCTTTCTG-3' (SEQ ID NO: 16) were used.

PCR reaction conditions employed herein comprise a reaction cycle repeated 25 times, each cycle consisting of a denaturation temperature of 94° C. for 1 min, an annealing temperature of 55° C. for 1 min and a DNA strand elongation temperature of 72° C. for 2 min.

(3) Preparation of Human Protein Disulfide Isomerase (hPDI*) by Removing Restriction Enzyme ApaL I Cleavage Site from Human Protein Disulfide Isomerase Gene 1) Preparation of DNA Fragment, hPDI-1

A blunt-ended DNA fragment, hPDI-1 was obtained by procedures similar to Example 1 (1) except for the following procedures.

A template DNA, 10 ng of a plasmid vector having hPDI DNA which had been obtained in Example 2 (2) incorporated therein was used.

As primers, a forward primer, 5'-GCCCCCGAGGAG-GAGGACCACGTCCTG-3' (SEQ ID NO: 15), and a reverse primer, 5'-TTTGACGGCCTCCACCTCGT-3' (SEQ ID NO: 17) were used.

PCR reaction conditions employed herein comprise a reaction cycle repeated 25 times, each cycle consisting of a denaturation temperature of 94° C. for 1 min, an annealing temperature of 55° C. for 1 min and a DNA strand elongation temperature of 72° C. for 1 min and 30 sec.

2) Preparation of DNA Fragment, hPDI-2

A blunt-ended DNA fragment, hPDI-2 was obtained by procedures similar to Example 1 (1) except for the following procedures.

As a template DNA, 10 ng of a plasmid vector having hPDI DNA which had been obtained in Example 2 (2) incorporated therein was used.

As primers, a forward primer, 5'-AGCTTCCCCACACT-CAAGTT-3' (SEQ ID NO: 18), and a reverse primer, 5'-TTACAGTTCATCTTTCACAGCTTTCTG-3' (SEQ ID NO: 16) were used.

PCR reaction conditions employed herein comprise a reaction cycle repeated 25 times, each cycle consisting of a denaturation temperature of 94° C. for 1 min, an annealing temperature of 55° C. for 1 min and a DNA strand elongation temperature of 72° C. for 15 sec.

3) Preparation of DNA Fragment, mhPDI-2

A blunt-ended and phosphorylated DNA fragment, mhPDI-2 was obtained by procedures similar to Example 1 (1) except for the following procedures.

As a template DNA, 10 ng of the PCR product DNA, hPDI-2, obtained in Example 2 (3) 2) was used.

As primers, a forward primer, 5'-GTTCATAGCTTC-CCCACACTCAAGTTC-3' (SEQ ID NO: 19), and a reverse primer, 5'-TTACAGTTCATCTTTCA-CAGCTTTCTG-3' (SEQ ID NO: 16) were used.

PCR reaction conditions employed herein comprise a reaction cycle repeated 25 times, each cycle consisting of a denaturation temperature of 94° C. for 1 min, an annealing temperature of 55° C. for 1 min and a DNA strand elongation temperature of 72° C. for 15 sec.

4) Preparation of DNA Fragment, hPDI*

A blunt-ended and phosphorylated DNA fragment, hPDI* was obtained by procedures similar to Example 1 (8) except for the following procedures.

A template DNA used for a first PCR reaction was prepared by mixing an appropriate amount of the DNA, hPDI-1, obtained in Example 2 (3) 1) and an appropriate amount of the DNA fragment, mhPDI-2, obtained in 3) to perform reaction at 16° C. for 30 min using a DNA ligation kit (TAKARA SHUZO CO., LTD).

As primers for a first PCR reaction, a forward primer, 5'-GCCCCCGAGGAGGAGGACCACGTCCTG-3' (SEQ ID NO: 15), and a reverse primer, 5'-TTACAGT-TCATCTTTCACAGCTTTCTG-3' (SEQ ID NO: 16) were used.

PCR reaction conditions employed herein comprise a reaction cycle repeated 25 times, each cycle consisting of a denaturation temperature of 94° C. for 1 min, an annealing temperature of 55° C. for 1 min and a DNA strand elongation temperature of 72° C. for 1 min and 30 sec.

(4) Preparation of Vector Having Fusion DNA, MWPsp-hPDI*, Incorporated Therein

1) Preparation of DNA Fragment, MWPsp

A blunt-ended DNA fragment, MWPsp, was obtained by procedures similar to Example 1 (1) except for the following procedures.

As a template DNA, 10 ng of an expression vector pNU211R2L5 of Bacillus brevis was used.

As primers, a forward primer, 5'-TATACTAGAGGAG-GAGAACAC-3' (SEQ ID NO: 20), and a reverse primer, 5'-TGCGAAAGCCATTGGAGCAAC-3' (SEQ ID NO: 21) were used.

PCR reaction conditions employed herein comprise a reaction cycle repeated 25 times, each cycle consisting of a denaturation temperature of 94° C. for 1 min, an annealing temperature of 55° C. for 1 min and a DNA strand elongation temperature of 72° C. for 30 sec.

2) Preparation of Vector Having Fusion DNA, MWPsp-hPDI*, Incorporated Therein

A vector having fusion DNA, MWPsp-hPDI*, incorporated therein was obtained by procedures similar to Example 1 (8) except for the following procedures.

A template DNA used for a first PCR reaction was prepared by mixing an appropriate amount of the DNA, MWPsp, obtained in Example 2 (4) 1) and an appropriate amount of the DNA fragment, hPDI*, obtained in Example 2 (3) to perform reaction at 16° C. for 30 min using a DNA ligation kit (TAKARA SHUZO CO., LTD).

As primers for a first PCR reaction, a forward primer, 5'-TATACTAGAGGAGGAGAACAC-3' (SEQ ID NO: 20), and a reverse primer, 5'-TTACAGT-TCATCTTTCACAGCTTTCTG-3' (SEQ ID NO: 16) were used.

PCR reaction conditions employed herein comprise a reaction cycle repeated 25 times, each cycle consisting of a denaturation temperature of 94° C. for 1 min, an annealing temperature of 55° C. for 1 min and a DNA strand elongation temperature of 72° C. for 1 min and 30 sec.

(5) Preparation of Vector Having Fusion DNA, MWPsp*-hPDI*, Incorporated Therein

MWPsp*-hPDI* prepared by fusing MWPsp*, which had been prepared by removing a cleavage site of a restriction enzyme ApaL I from MWPsp, with hPDI* was obtained as follows.

1) Preparation of DNA Fragment, MWPsp-1

A blunt-ended DNA fragment, MWPsp-1, was obtained by procedures similar to Example 1 (1) except for the following procedures.

As a template DNA, 10 ng of a vector having a fusion DNA, MWPsp-hPDI*, incorporated therein was used.

As primers, a forward primer, 5'-TATACTAGAGGAG-GAGAACAC-3' (SEQ ID NO: 20), and a reverse primer, 5'-GCTAGCCAATACACTGTTAAC-3' (SEQ ID NO: 22) were used.

PCR reaction conditions employed herein comprise a reaction cycle repeated 25 times, each cycle consisting of a denaturation temperature of 94° C. for 1 min, an annealing temperature of 53° C. for 1 min and a DNA strand elongation temperature of 72° C. for 15 sec.

2) Preparation of DNA Fragment, MWPsp-2-hPDI*

A blunt-ended DNA fragment, MWPsp-2-hPDI*, was obtained by procedures similar to Example 1 (1) except for the following procedures.

As a template DNA, 10 ng of a vector having a fusion DNA, MWPsp-hPDI*, incorporated therein was used.

As primers, a forward primer, 5'-GCTCTCGCACT-TACTGTTGCTCCA-3' (SEQ ID NO: 23), and a reverse primer, 5'-TTACAGTTCATCTTTCA-CAGCTTTCT3' (SEQ In N 16) were used.

PCR reaction conditions employed herein comprise a reaction cycle repeated 25 times, each cycle consisting of a denaturation temperature of 94° C. for 1 min, an annealing temperature of 53° C. for 1 min and a DNA strand elongation temperature of 72° C. for 1 min and 30 sec.

3) Preparation of Vector Having MWPsp*-hPDI* Incorporated Therein

A vector having fusion DNA, MWPsp*-hPDI*, incorporated therein was obtained by procedures similar to Example 1 (8) except for the following procedures.

A template DNA used for a first PCR reaction was prepared by mixing an appropriate amount of the DNA, MWPsp-1 obtained in Example 2 (5) 1), and an appropriate amount of the DNA fragment, MWPsp-2-hPDI*, obtained in 2) to perform reaction at 16° C. for 30 min using a DNA ligation kit (TAKARA SHUZO CO., LTD).

As primers for a first PCR reaction, a forward primer, 5'-TATACTAGAGGAGGAGAACAC-3' (SEQ ID NO: 20), and a reverse primer, 5'-TTACAGT-TCATCTTTCACAGCTTTCTG-3' (SEQ ID NO: 16) were used.

PCR reaction conditions employed herein comprise a reaction cycle repeated 25 times, each cycle consisting of a denaturation temperature of 94° C. for 1 min, an annealing temperature of 55° C. for 1 min and a DNA strand elongation temperature of 72° C. for 2 min.

(6) Preparation of Vector Having MWPsp-MWPmp9-GSLQPR-B Chain-RGHRP-Linker-PR-A Chain-MWPsp*-hPDI* Incorporated Therein 1) Preparation of DNA Fragment, MWPsp*-hPDI*

A blunt-ended and phosphorylated DNA fragment, MWPsp*-hPDI*, was obtained by procedures similar to Example 1 (1) except for the following procedures.

As a template DNA, 10 ng of a vector having MWPsp*-hPDI* obtained in (5) 4) incorporated therein was used.

As primers, a forward primer, 5'-TATACTAGAGGAG-GAGAACAC-3' (SEQ ID NO: 20), and a reverse primer, 5'-TTACAGTTCATCTTTCA-CAGCTTTCTG-3' (SEQ ID NO: 16) were used.

PCR reaction conditions employed herein comprise a reaction cycle repeated 25 times, each cycle consisting of a denaturation temperature of 94° C. for 1 min, an annealing temperature of 55° C. for 1 min and a DNA strand elongation temperature of 72° C. for 2 min.

2) Preparation of Vector Having MWPsp-MWPmp9-GSLQPR-B Chain-RGHRP-Linker-PR-A Chain-MWPsp*-hPDI* Incorporated Therein A vector having a fusion DNA, MWPsp-MWPmp9-GSLQPR-B chain-RGHRP-Linker-PR-A chain-MWPsp*-hPDI*, incorporated therein was obtained by procedures similar to Example 1 (8) except for the following procedures.

A template DNA used for a first PCR reaction was prepared by mixing an appropriate amount of the DNA, MWPsp-MWPmp9-GSLQPR-B chain-RGHRP-Linker-PR-A chain, obtained in Example 2 (1), and an appropriate amount of the DNA fragment, MWPsp*-hPDI*, obtained in (6) 1) to perform reaction at 16° C. for 30 mil using a DNA ligation kit (TAKARA. SHUZO CO., LTD).

As primers for a first PCR reaction, a forward primer, 5'-ACACGCGCTTGCAGGATTCG-3' (SEQ ID NO: 1), and a reverse primer, 5'-TTACAGT-TCATCTTTCACAGCTTTCTG-3' (SEQ ID NO: 16) were used.

PCR reaction conditions employed herein comprise a reaction cycle repeated 25 times, each cycle consisting of a denaturation temperature of 94° C. for 1 min, an annealing temperature of 55° C. for 1 min and a DNA strand elongation temperature of 72° C. for 2 min and 30 sec.

Example 3

Expression and Secretion of Fusion DNA (1) Amino Acid and Nucleotide Sequences of Fusion DNA The amino acid sequence and the nucleotide sequence of the fusion DNA obtained in Example 1 corresponding to SEQ ID NOS: 24 and 25, respectively, are shown in FIG. 1A; the amino acid sequence and the nucleotide sequence (SEQ ID NO: 26) of the fusion DNA obtained in Example 2 are shown in FIG. 1B; and the amino acid sequence of the fusion protein, MWPsp*-hPDI* (FIG. 1B), is shown in SEQ ID NO: 27.

(2) Expression and Secretion of Fusion DNA

A fusion protein encoded by the fusion DNAs obtained in Examples 1 and 2 was expressed. A method for incorporating the fusion DNAs into an expression vector is shown in FIG. 2.

Specifically, the vector pmPINS, pmPINS~hPDI* having the above fusion DNAs incorporated therein was treated with restriction enzymes ApaL I and Hind III, and then subjected to 0.8% agarose electrophoresis, thereby excising DNA fragments containing each fusion DNA. Appropriate amounts of the excised fusion DNAs and of an expression vector pNU211R2L5 for *Bacillus brevis* (Japanese Patent Application Laying-Open (Kokai) No. 7-170984) that had been cut with ApaL I and Hind III were mixed to perform reaction at 16° C. for 30 min using a DNA ligation kit (TAKARA SHUZO CO., LTD.), thereby incorporating the fusion DNAs into the expression vector. As described above, the expression vector pNU-mPINS, pNU-mPINS~hPDI* containing each fusion DNA was obtained. *Bacillus brevis* strain 47-5 (FERM BP-1664) was transformed with these expression vectors by a known method (Methods in Enzymol., 217: 23–33, 1993), inoculated on T2 agar medium [polypeptone (1%), meat extract (0.5%), yeast extract (0.2%), uracil (0.1 mg/mL), glucose (1%), erythromycin (10 μg/mL) and agar (1.5%), pH 7], thereby obtaining transformants.

The transformants were cultured on T2 media that had been prepared by removing agar from T2 agar medium at 37° C. for 1 day. Then, plasmid DNA was purified by a known method (Molecular Cloning $2^{nd}$ ed., A Laboratory Manual, Cold Spring Harbor Laboratory (1989)), and then treated with ApaL I and Hind III, so that incorporation of the fusion DNA was confirmed.

Example 4

Demonstration by SDS-PAGE of an Increase in the Amount of Monomeric Fusion Protein Containing Insulin A fusion protein which contains insulin having disulfide bonds formed within its molecule is a monomer. Here, an increase in the amount of monomers was examined with SDS-PAGE under non-reduction conditions. Transformants that had been confirmed to contain incorporated DNAs encoding the fusion protein containing insulin were cultured on T2 medium at 37° C. for 1 day. Subsequently, the cell suspension solution was added at a proportion of 1/1000 volume to a medium [polypeptone (3%), yeast extract (0.4%), glucose (3%), $MgSO_4 \cdot 7H_2O$ (0.01%), $MnSO_4 \cdot 4H_2O$ (0.001%) and erythromycin (10 µg/mL), pH 8] and then shake-cultured at 30° C. for 4 days.

Figure 3:
FIG. 3 shows a picture of electrophoresis of a medium taken after transformants were cultured. In the figure, lane 1 indicates a marker peptide; lane 2 pNU-mPINS (nonreduction), lane 3 pNU-mPINS-hPDI* (nonreduction), lane 4 pNU-mPINS (reduction), and lane 5 pNU-mPINS-hPDI* (reduction).

After culturing, the media were centrifuged at 15,000 rpm for 2 min to obtain the culture supernatant. Then, the protein was analyzed by electrophoresis using a known method (Laemmli, U. K., Nature, 227: 680–685 (1970)). Specifically, 2 µL of a buffer under non-reduction conditions [125 mol/L Tris-HCl (pH 6.8), 20% glycerol, 4% SDS] or a buffer under reduction conditions [125 mmol/L Tris-HCl (pH 6.8), 20% glycerol, 4% SDS, 10% 2-mercaptoethanol] was added to 18 µL of the culture supernatant. The mixture was boiled for 5 min, and then supplemented with 4 µL of a loading buffer [250 mmol/L Tris-HCl (pH 6.5), 50% glycerol, 0.5% BPB]. The solution was applied to a commercially available 15/25% SDS polyacrylamide gel (Daiichi Pure Chemicals, Japan) to perform electrophoresis (electrophoresis buffer: 100 mmol/L Tris, 100 mmol/L Tricine, 0.1% SDS). After electrophoresis, Coomassie staining was performed so as to examine the amount of monomers of a target fusion protein. As shown in FIG. 3, though the amount of the fusion protein (arrow B) containing insulin expressed and secreted from pNU-mPINS and that from pNU-mPINS-hPDI* were almost the same (predicted from the SDS-PAGE image of lanes 4 and 5 under reduction conditions), the amount of the monomer of the fusion protein expressed and secreted from pNU-mPINS-hPDI* that had been designed to allow co-existence in the media of the fusion protein containing insulin and protein disulfide isomerase (arrow A) was clearly increased (lane 3).

Example 5

Figure 4:
FIG. 4 shows a photograph of western blotting of a medium take after transformants were cultured. In the figure, lane 1 indicates pNU-mPINS (nonreduction); lane 2 pNU-mPINS-hPDI* (nonreduction), lane 3 pNU-mPINS (reduction), and lane 4 pNU-mPINS-hPDI* (reduction).
Figure 4:

Demonstration by Western Blotting of an Increase in the Amount of Monomeric Fusion Protein Containing Insulin The amount of the monomeric fusion proteins containing insulin was increased or decreased using antibodies for C peptide (Linker portion). Similar to Example 3, bacteria transformed with pNU-mPINS or pNU-mPINS-hPDI* vector were cultured. The resulting media were centrifuged at 15,000 rpm for 2 min. Then, 1 µL of the culture supernatant was subjected to electrophoresis under reduction or non-reduction conditions similar to Example 3. Next, the product was blotted electrically onto a nitrocellulose membrane by a known method (Towbin, H. et al., 76: 4350–4354 (1979)). Subsequently, the membrane was immersed in a 5% skim milk solution [5% skim milk, 20 mmol/L Tris-HCl (pH 7.4), 150 mM NaCl, 0.1% Tween 20] for 1 hour, immersed for 30 min in rabbit anti-C-peptide antibody (LINCO RESEARCH) diluted 2000-fold with a buffer [20 n-mol/L Tris-HCl (pH 7.4), 150 mmol/L NaCl, 0.1% Tween 20] while being shaken, washed 3 times with the buffer for 10 min while being shaken, and then immersed in peroxidase-labeled anti-rabbit IgG antibodies (E-Y Laboratories) diluted 2000-fold with the buffer for 30 min while being shaken. After immersion, the membrane was washed 3 times with the buffer for 10 min while being shaken, and then increases and decreases in the amount of the monomeric fusion protein containing insulin were examined using an ECL detection kit (Amersham-Pharmacia). This was performed by a method according to the kit's instructions. As shown in FIG. 4, under reduction conditions, almost the same amount of the monomeric fusion protein containing insulin was confirmed to be present in both pNU-mPINS (lane 3) and pNU-mPINS-hPDI* (lane 4). In contrast, under non-reduction conditions, the amount of the monomeric fusion protein was greater in pNU-mPINS-hPDI* (lane 2) than the amount in pNU-mPINS (lane 1). In pNU-mPINS, a smear yielded by reaction was observed in the high molecular range, suggesting that the fusion protein formed non-specific disulfide bonds with high polymers. That is, regarding pNU-mPINS-hPDI* wherein protein disulfide isomerase and the fusion protein containing insulin co-expressed, it was shown that a smaller number of non-specific disulfide bonds were formed with high polymers, and the formation of the monomers of the fusion proteins was enhanced.

Example 6

Figure 5:
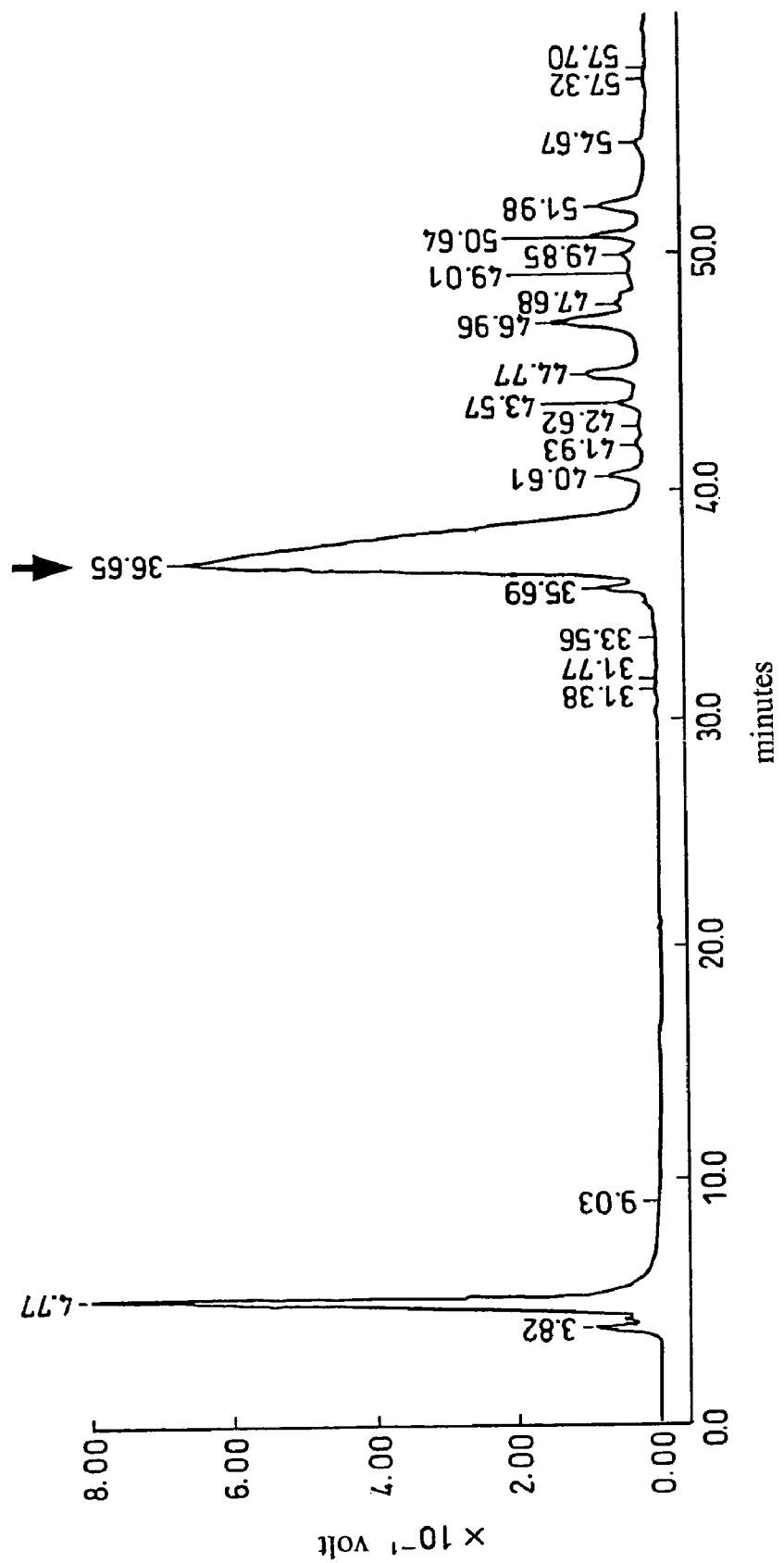
FIG. 5 shows an HPLC elution pattern for a fusion protein, MWPmp9-GSLQPR-B chain-RGHRP-Linker-PR-A chain.

Demonstration by HPLC of Increase in the Amount of Monomeric Fusion Protein Containing Insulin Bacteria transformed with pNU-mPINS, pNU-mPINS-hPDI* were cultured at 37° C. for 1 day. The cell suspension solution 50 µL was added to 50 mL of a medium [polypeptone (3%), yeast extract (0.4%), glucose (3%), $MgSO_4 \cdot 7H_2O$ (0.01%), $MnSO_4 \cdot 4H_2O$ (0.001%), erythromycin (10 µg/mL), pH 8], put into a 500 mL Erlenmeyer flask (6 flasks in total), and then shake-cultured at 30° C. for 4 days. The media were centrifuged at 9,000 rpm for 20 min, and then the resulting supernatant was dialyzed with a buffer at 4° C. (20 mmol/L Na—$PO_4$, 150 mmol/L, pH 8). Subsequently, the product was centrifuged at 10,000 rpm for 20 min, the resulting supernatant was applied to a Ni-chelate column (5×10 cm, Pharmacia), and then the above buffer was added with 60 mmol/L imidazole, thereby eluting target fusion proteins. The eluted product was dialyzed against 20 mmol/L Tris and 1 mmol/L EDTA (pH 8.0), supplemented with urea (final concentration of 1 mol/L) and 2-propanol (final concentration of 20%), and then applied to a Q-Sepharose XL column (1.6×10 cm) (Pharmacia). The product was sufficiently equilibrated with a buffer (20 mmol/L Tris, 1 mmol/L EDTA, 1 mol/L Urea, 20% 2-propanol, pH 8), and then eluted with a gradient of the buffer that was created using a solution containing 1M NaCl. Fractions eluted with 160 mmol/L to 200 mmol/L NaCl were collected, adjusted to pH 3 using 1N HCl, concentrated using an ultrafilter with a fraction molecular weight of 3,000, and then applied to Vydac214TP54 (C4 column, 4.6×250 mm, Cypress) to be purified by HPLC. The purified product was equilibrated with 25% acetonitrile and 0.1% TFA solution, and then eluted with a gradient that was created using 33% acetonitrile and 0.1% TFA solution. FIG. 5 shows the elution pattern. The fraction eluted with 30–31% acetonitrile (indicated with an arrow), namely the monomer of the fusion protein containing insulin, was dried and solidified by centrifugation and concentration. Table 1 shows the molar ratio (mol %) of the amino acid composition and total amount of the monomer of the-fusion protein containing insulin that was obtained from pNU-mPINS or pNU-mPINS-hPDI*. The total amount of the monomer of the fusion protein containing insulin in pNU-mPINS-hPDI* was increased to about 4.5-fold more than the total amount of pNU-mPINS. Table 1 also shows the molar ratio (mol %) of the amino acid composition and the total amount of the monomer of the fusion protein obtained from the transformant of MVPmp9GSLQPR-B chain-RGHRP-Linker-PR-A chain, pNU-mPINS or pNU-mPINS-hPDI*.

after treating with thrombin was applied to Mightysil RP4 (20×250 mm, Cica-MERCK), equilibrated with 25% acetonitrile and 0.1% TFA solution, and then eluted with a gradient that was created using 35% acetonitrile and 0.1% TFA solution.

Fractions eluted with 30–31% acetonitrile were centrifuged and concentrated. The dried and solidified fractions were subjected to the following experiment.

The dried and solidified insulin-Arg was dissolved in an appropriate amount of 0.1% TFA, added with 0.1 mol/L Tris buffer (pH 8) to 1 mg/mL, and then added with a carbox-

TABLE 1

|  | pNU-mPINS | | | pNU-mPINS-hPDI* | | | theoretical value | |
| --- | --- | --- | --- | --- | --- | --- | --- | --- |
|  | nmole | mol % | nmol/mol % | nmole | mol % | nmol/mol % | residue | mol % |
| Asp | 4.916 | 4.06% | 1.23 | 11.082 | 4.01% | 2.771 | 4 | 3.85% |
| Thr | 6.872 | 5.67% | 1.15 | 15.466 | 5.59% | 2.578 | 6 | 5.77% |
| Ser | 6.477 | 5.35% | 1.08 | 14.953 | 5.41% | 2.492 | 6 | 5.77% |
| Glu | 21.833 | 18.02% | 1.21 | 49.927 | 18.05% | 2.774 | 18 | 17.31% |
| Pro | 7.531 | 6.22% | 1.26 | 17.570 | 6.35% | 2.928 | 6 | 5.77% |
| Gly | 15.871 | 13.10% | 1.22 | 36.537 | 13.21% | 2.811 | 13 | 12.50% |
| Ala | 9.977 | 8.24% | 1.25 | 22.737 | 8.22% | 2.842 | 8 | 7.69% |
| Cys1/2 *1 | 3.422 | 2.82% |  | 8.120 | 2.94% |  | 6 | 5.77% |
| Val | 6.772 | 5.59% | 1.13 | 15.312 | 5.54% | 2.552 | 6 | 5.77% |
| Met |  |  |  |  |  |  |  |  |
| Ile | 2.077 | 1.71% | 1.04 | 4.716 | 1.70% | 2.358 | 2 | 1.92% |
| Leu | 16.346 | 13.49% | 1.26 | 37.401 | 13.52% | 2.877 | 13 | 12.50% |
| Tyr | 4.662 | 3.85% | 1.17 | 10.851 | 3.92% | 2.713 | 4 | 3.85% |
| Phe | 3.711 | 3.06% | 1.24 | 8.305 | 3.00% | 2.768 | 3 | 2.88% |
| Lys | 1.231 | 1.02% | 1.23 | 2.651 | 0.96% | 2.651 | 1 | 0.96% |
| His | 3.450 | 2.85% | 1.15 | 7.426 | 2.68% | 2.475 | 3 | 2.88% |
| Trp |  |  |  |  |  |  |  |  |
| Arg | 5.987 | 4.94% | 1.20 | 13.570 | 4.91% | 2.714 | 5 | 4.81% |
| total | 121.135 | 100.00% | 1.19 | 276.624 | 100.00% | 2.687 | 104 | 100.00% |
|  |  |  | 790.91 nmol |  |  | 3582.53 nmol |  |  |
| collected amount |  |  | 8.81 mg |  |  | 39.91 mg |  |  |

*1 no correction

Example 7

Demonstration of Correct Disulfide Bond Formation

A comparison of peptide mappings was made between the fusion protein, MWPmp9-GSLQPR-B chain-RGHRP-Linker-PR-A chain, which had been converted to insulin with thrombin and carboxypeptidase B as shown below, and of commercially available insulin. Thus, it was demonstrated that correct disulfide bonds had been formed. FIG. 6 shows a schematic diagram of conversion of the fusion protein to insulin using thrombin and carboxypeptidase B.

The dried and solidified fusion protein, MWPmp9-GSLQPR-B chain-RGHRP-Linker-PR-A chain, obtained in Example 6 was dissolved in an appropriate amount of 0.1% TFA, and then added with 0.1 mol/L Tris buffer (pH 8) to 20 nmol/mL. The mixture was cooled to 4° C., added with a thrombin solution (250 μmol/mL, substrate:enzyme=25:1 (molar ratio)), and 9 hours later added with an appropriate amount of 10% trifluoroacetic acid (TFA) to pH 2 to stop the reaction. Thrombin used herein was prepared by re-purifying official thrombin (ITOHAM FOODS INC. Japan) with Macro Prep CM (Bio Rad) and Lysine Sepharose 4B (Pharmacia).

To purify insulin-Arg having Arg at the C-terminus of the B chain cleaved with thrombin by reverse phase HPLC, the above reaction solution for which reaction had been ceased ypeptidase B solution (substrate:enzyme=500:1 (molar ratio), Sigma, 4.7 mg/mL) for treatment at 25° C. for 12 hours. Then, an appropriate amount of 10% TFA was added to pH 2 to stop the reaction. To purify insulin from the reaction solution for which reaction had been ceased, reverse phase HPLC was performed similar to that employed for purification of the above insulin-Arg.

5 nmole of the obtained insulin (the present invention) and a commercially available insulin, Novolin 40 needle (hereinafter referred to as Novolin) (Novo Nordisk Pharma), were each dissolved in 50 μL of 0.1 mol/L ammonium bicarbonate, 2 mmol/L EDTA solution (pH 7.8). 1.35 mL of an aqueous solution V8 protease (Wako Pure Chemical Industries, Ltd., Japan, 2 μg/mL) was added to the mixture for reaction to proceed at 25° C. for 24 hours. Then, 1% TFA was added to PH2 to stop the reaction. Next, the reaction solution for which reaction had been ceased was applied to Vydac218TP54 (4.6×250 mm, C18 column), equilibrated with 5% acetonitrile and 0.1% TFA solution, and then eluted with a gradient that was created using 35% acetonitrile and 0.1% TFA solution. FIG. 7 shows the elution pattern. The insulin of the present invention and Novolin (commercially available insulin) showed similar patterns. It was concluded that the disulfide bond mechanisms of both insulins are identical.

Industrial Applicability

The formation of correct disulfide bonds of a polypeptide having disulfide bonds expressed and secreted in an expression system of the bacteria of the genus *Bacillus* is drastically enhanced according to the present invention. This can lead to drastically increased yields of a gene recombinant polypeptide.

Sequence Listing Free Text

SEQ ID NO: 1 Description of artificial sequence: a primer for PCR
SEQ ID NO: 2 Description of artificial sequence: a primer for PCR
SEQ ID NO: 3 Description of artificial sequence: a primer for PCR
SEQ ID NO: 4 Description of artificial sequence: a primer for PCR
SEQ ID NO: 5 Description of artificial sequence: a primer for PCR
SEQ ID NO: 6 Description of artificial sequence: a primer for PCR
SEQ ID NO: 7 Description of artificial sequence: a primer for PCR
SEQ ID NO: 8 Description of artificial sequence: a primer for PCR
SEQ ID NO: 9 Description of artificial sequence: a primer for PCR
SEQ ID NO: 10 Description of artificial sequence: a primer for PCR
SEQ ID NO: 11 Description of artificial sequence: a primer for PCR
SEQ ID NO: 12 Description of artificial sequence: a primer for PCR
SEQ ID NO: 13 Description of artificial sequence: a primer for PCR
SEQ ID NO: 14 Description of artificial sequence: a primer for PCR
SEQ ID NO: 15 Description of artificial sequence: a primer for PCR
SEQ ID NO: 16 Description of artificial sequence: a primer for PCR
SEQ ID NO: 17 Description of artificial sequence: a primer for PCR
SEQ ID NO: 18 Description of artificial sequence: a primer for PCR
SEQ ID NO: 19 Description of artificial sequence: a primer for PCR
SEQ ID NO: 20 Description of artificial sequence: a primer for PCR
SEQ ID NO: 21 Description of artificial sequence: a primer for PCR
SEQ ID NO: 22 Description of artificial sequence: a primer for PCR
SEQ ID NO: 23 Description of artificial sequence: a primer for PCR
SEQ ID NO: 24 Description of artificial sequence: sequence of fusion protein, MWPsp-MWPmp9-GSLQPR-B chain-RGHRP-Linker-PR-A chain
SEQ ID NO: 25 Description of artificial sequence: DNA sequence encoding fusion protein, MWPsp-MWPmp9-GSLQPR-B chain-RGHRP-Linker-PR-A chain
SEQ ID NO: 26 Description of artificial sequence: DNA sequence encoding fusion protein, MWPsp-MWPmp9-GSLQPR-B chain-RGHRP-Linker PR-Achain-MWPsp*-hPDI*
SEQ ID NO: 27 Description of artificial sequence: sequence of fusion protein, MWPsp*-hPDI*

Various publications are cited in the above description. All of these publications and patent applications are incorporated herein by reference. Further, the present invention may be modified or changed in various ways within a scope equivalent to that of the inventions described in the scope for attached claims, and all the equivalents are included within the scope of the present invention.

The invention claimed is:

1. A DNA which enables co-expression of a protein disulfide isomerase and a polypeptide having disulfide bonds,
comprising at least one promoter required for gene expression, two identical or different Shine-Dalgarno sequences (SD), two identical or different sequences encoding signal peptides of cell wall proteins (CWP) of a bacterium of the genus Bacillus (CWPsp), a gene encoding a polypeptide having disulfide bonds which is a fusion protein comprising human insulin, and a gene encoding protein disulfide isomerase (PDI) that are ligated to each other as represented by the following formula:

5'-Promoter-SD-CWPsp-$X_1$-(Promoter)n-SD-CWPsp-$X_2$-3', wherein $X_1$=fusion protein and $X_2$=PDI, or $X_1$=PDI and $X_2$=fusion protein, and n=0 or 1, wherein if n=1 then the first promoter and the second promoter are identical or different and wherein if n=0, there is only one promoter,
wherein the fusion protein comprising a human insulin is represented by the following formula:
MWPmp9-GSLQPR-B chain-RGHRP-Linker-PR-A chain,
wherein MWPmp9 represents 9 amino acids from the N terminus of a middle-wall mature protein of bacteria of the genus Bacillus; GSLQPR, RGHRP and PR each represents amino acids 30–35, amino acids 66–70 and amino acids 34–35 of SEQ ID NO:24, A chain and B chain respectively represent the A chain and B chain of human insulin; and Linker represents a linker consisting of any amino acids.

2. The DNA of claim 1, wherein the promoter is derived from a bacterium of the genus Bacillus.

3. The DNA of claim 2, wherein the promoter is derived from a gene encoding Bacillus CWP.

4. The DNA of claim 3, wherein CWP is a middle wall protein (MWP).

5. The DNA of claim 1, wherein the protein disulfide isomerase is derived from a human.

6. A vector which comprises the DNA according to claim 1.

7. A bacterium of the genus Bacillus which is transformed with the vector of claim 6.

8. The bacterium of claim 7, wherein the bacterium of the genus Bacillus is Bacillus brevis.

9. A process for producing a polypeptide having disulfide bonds, which comprises:
introducing the vector according to claim 6 into a bacterium of the genus Bacillus;
culturing the obtained transformed bacterium in a medium;
co-expressing a protein disulfide isomerase and the polypeptide having one or more disulfide bonds, thereby secreting together extracellularly; and
collecting the polypeptide having correct disulfide bonds formed by the action of the protein disulfide isomerase.

10. The process of claim 9, which further comprises the steps of:
generating a polypeptide having correct disulfide bonds as a fusion protein; and
treating the obtained fusion protein with protease to obtain the polypeptide.

11. The DNA of claim 5, wherein the promoter is derived from a bacterium of the genus Bacillus.

12. The DNA of claim 11, wherein the promoter is derived from a gene encoding Bacillus CWP.

13. The DNA of claim 12, wherein CWP is a middle wall protein (MWP).

14. A vector which comprises the DNA according to claim 5.

15. A bacterium of the genus Bacillus which is transformed with the vector of claim 14.

16. The bacterium of claim 15, wherein the bacterium of the genus Bacillus is Bacillus brevis.

17. A process for producing a polypeptide having disulfide bonds, which comprises:
introducing the vector according to claim 14 into a bacterium of the genus Bacillus;
culturing the obtained transformed bacterium in a medium;
co-expressing a protein disulfide isomerase and the polypeptide having one or more disulfide bonds, thereby secreting together extracellularly; and
collecting the polypeptide having correct disulfide bonds formed by the action of the protein disulfide isomerase.

18. The process of claim 17, which further comprises the steps of:
generating a polypeptide having correct disulfide bonds as a fusion protein; and
treating the obtained fusion protein with protease to obtain the polypeptide.

* * * * *

SEQUENCE LISTING

```
<160> NUMBER OF SEQ ID NOS: 27

<210> SEQ ID NO 1
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 1
acacgcgctt gcaggattcg                                              20

<210> SEQ ID NO 2
<211> LENGTH: 18
<212> TYPE: DNA
<213> ORGANISM: ARTIFICIAL SEQUENCE
<220> FEATURE:
<223> OTHER INFORMATION: SYNTHETIC DNA

<400> SEQUENCE: 2
agctgtagta gttgctgc                                                18

<210> SEQ ID NO 3
<211> LENGTH: 19
<212> TYPE: DNA
<213> ORGANISM: ARTIFICIAL SEQUENCE
<220> FEATURE:
```

-continued

<223> OTHER INFORMATION: SYNTHETIC DNA

<400> SEQUENCE: 3
atggccctgt ggatgcgcc                                           19

<210> SEQ ID NO 4
<211> LENGTH: 19
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
ctagttgcag tagttctcc                                           19

<210> SEQ ID NO 5
<211> LENGTH: 18
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
tttgtgaacc aacacctg                                            18

<210> SEQ ID NO 6
<211> LENGTH: 19
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
ctagttgcag tagttctcc                                           19

<210> SEQ ID NO 7
<211> LENGTH: 36
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
ggttccttgc aacctcgttt tgtgaaccaa cacctg                        36

<210> SEQ ID NO 8
<211> LENGTH: 18
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
gcgggtcttg ggtgtgta                                            18

<210> SEQ ID NO 9
<211> LENGTH: 18
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
gaggcagagg acctgcag                                            18

```
<210> SEQ ID NO 10
<211> LENGTH: 18
<212> TYPE: DNA
<213> ORGANISM: ARTIFICIAL SEQUENCE
<220> FEATURE:
<223> OTHER INFORMATION: SYNTHETIC DNA

<400> SEQUENCE: 10
ctgcagggac ccctccag                                                    18

<210> SEQ ID NO 11
<211> LENGTH: 36
<212> TYPE: DNA
<213> ORGANISM: ARTIFICIAL SEQUENCE
<220> FEATURE:
<223> OTHER INFORMATION: SYNTHETIC DNA

<400> SEQUENCE: 11
ggtcaccgtc cagaggcaga ggacctgcag gtgggg                                36

<210> SEQ ID NO 12
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 12
ggcattgtgg aacaatgctg t                                                21

<210> SEQ ID NO 13
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 13
ctagttgcag tagttctcca gctggta                                          27

<210> SEQ ID NO 14
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 14
ccacgtggca ttgtggaaca atgctgts                                         28

<210> SEQ ID NO 15
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 15
gcccccgagg aggaggacca cgtcctg                                          27

<210> SEQ ID NO 16
<211> LENGTH: 27
<212> TYPE: DNA
<213> ORGANISM: ARTIFICIAL SEQUENCE
<220> FEATURE:
<223> OTHER INFORMATION: SYNTHETIC DNA
```

```
<400> SEQUENCE: 16
ttacagttca tctttcacag ctttctg                                    27

<210> SEQ ID NO 17
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 17
tttgacggcc tccacctcgt                                            20

<210> SEQ ID NO 18
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 18
agcttcccca cactcaagtt                                            20

<210> SEQ ID NO 19
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 19
gttcatagct tccccacact caagttc                                    27

<210> SEQ ID NO 20
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 20
tatactagag gaggagaaca c                                          21

<210> SEQ ID NO 21
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 21
tgcgaaagcc attggagcaa c                                          21

<210> SEQ ID NO 22
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 22
gctagccaat acactgttaa c                                          21

<210> SEQ ID NO 23
<211> LENGTH: 24
```

```
<212> TYPE: DNA
<213> ORGANISM: ARTIFICIAL SEQUENCE
<220> FEATURE:
<223> OTHER INFORMATION: SYNTHETIC DNA

<400> SEQUENCE: 23
gctctcgcac ttactgttgc tcca                                          24

<210> SEQ ID NO 24
<211> LENGTH: 124
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 24

Val Val Asn Ser Val Leu Ala Ser Ala Leu Ala Leu Thr Val Ala Pro
 1               5                  10                  15

Met Ala Phe Ala Ala Glu Glu Ala Ala Thr Thr Thr Ala Gly Ser Leu
            20                  25                  30

Gln Pro Arg Phe Val Asn Gln His Leu Cys Gly Ser His Leu Val Glu
        35                  40                  45

Ala Leu Tyr Leu Val Cys Gly Glu Arg Gly Phe Phe Tyr Thr Pro Lys
    50                  55                  60

Thr Arg Gly His Arg Pro Glu Ala Glu Asp Leu Gln Val Gly Gln Val
65                  70                  75                  80

Glu Leu Gly Gly Gly Pro Gly Ala Gly Ser Leu Gln Pro Leu Ala Leu
                85                  90                  95

Glu Gly Ser Leu Gln Pro Arg Gly Ile Val Glu Gln Cys Cys Thr Ser
            100                 105                 110

Ile Cys Ser Leu Tyr Gln Leu Glu Asn Tyr Cys Asn
        115                 120

<210> SEQ ID NO 25
<211> LENGTH: 375
<212> TYPE: DNA
<213> ORGANISM: ARTIFICIAL SEQUENCE
<220> FEATURE:
<223> OTHER INFORMATION: SYNTHETIC DNA

<400> SEQUENCE: 25
gtcgttaaca gtgtattggc tagtgcactc gcacttactg ttgctccaat ggctttcgca    60
gcagaagaag cagcaactac tacagctggg tccctgcagc cacgttttgt gaaccaacac   120
ctgtgcggct cacacctggt ggaagctctc tacctagtgt gcggggaaag aggcttcttc   180
tacacaccca gacccgcgg tcaccgtcca gaggcagagg acctgcaggt ggggcaggtg   240
gagctgggcg ggggccctgg tgcaggcagc ctgcagccct ggcccctgga ggggtccctg   300
cagccacgtg gcattgtgga acaatgctgt accagcatct gctccctcta ccagctggag   360
aactactgca actag                                                   375

<210> SEQ ID NO 26
<211> LENGTH: 1944
<212> TYPE: DNA
<213> ORGANISM: ARTIFICIAL SEQUENCE
<220> FEATURE:
<223> OTHER INFORMATION: SYNTHETIC DNA

<400> SEQUENCE: 26
gtcgttaaca gtgtattggc tagtgcactc gcacttactg ttgctccaat ggctttcgca    60
```

-continued

| | |
|---|---|
| gcagaagaag cagcaactac tacagctggg tccctgcagc cacgttttgt gaaccaacac | 120 |
| ctgtgcggct cacacctggt ggaagctctc tacctagtgt gcggggaaag aggcttcttc | 180 |
| tacacaccca agacccgcgg tcaccgtcca gaggcagagg acctgcaggt ggggcaggtg | 240 |
| gagctgggcg ggggccctgg tgcaggcagc ctgcagccct tggccctgga ggggtccctg | 300 |
| cagccacgtg gcattgtgga acaatgctgt accagcatct gctccctcta ccagctggag | 360 |
| aactactgca actagtatac tagaggagga gaacacaagg ttatgaaaaa ggtcgttaac | 420 |
| agtgtattgg ctagcgctct cgcacttact gttgctccaa tggctttcgc agcccccgag | 480 |
| gaggaggacc acgtcctggt gctgcggaaa agcaacttcg cggaggcgct ggcggcccac | 540 |
| aagtacctgc tggtggagtt ctatgcccct tggtgtggcc actgcaaggc tctggcccct | 600 |
| gagtatgcca agccgctgg gaagctgaag gcagaaggtt ccgagatcag gttggccaag | 660 |
| gtggacgcca cggaggagtc tgacctggcc cagcagtacg cgtgcgcgg ctatcccacc | 720 |
| atcaagttct tcaggaatgg agacacggct ccccccaagg aatatacagc tggcagagag | 780 |
| gctgatgaca tcgtgaactg gctgaagaag cgcacgggcc cggctgccac caccctgcct | 840 |
| gacggcgcag ctgcagagtc cttggtggag tccagcgagg tggctgtcat cggcttcttc | 900 |
| aaggacgtgg agtcggactc tgccaagcag tttttgcagg cagcagaggc catcgatgac | 960 |
| ataccatttg ggatcacttc caacagtgac gtgttctcca ataccagct cgacaaagat | 1020 |
| ggggttgtcc tctttaagaa gtttgatgaa ggccggaaca ctttgaaagg ggaggtcacc | 1080 |
| aaggagaacc tgctggactt tatcaaacac aaccagctgc cccttgtcat cgagttcacc | 1140 |
| gagcagacag ccccgaagat ttttggaggt gaaatcaaga ctcacatcct gctgttcttg | 1200 |
| cccaagagtg tgtctgacta tgacggcaaa ctgagcaact tcaaaacagc agccgagagc | 1260 |
| ttcaagggca agatcctgtt catcttcatc gacagcgacc acaccgacaa ccagcgcatc | 1320 |
| ctcgagttct ttggcctgaa gaaggaagag tgccggccg tgcgcctcat caccctggag | 1380 |
| gaggagatga ccaagtacaa gcccgaatcg gaggagctga cggcagagag gatcacagag | 1440 |
| ttctgccacc gcttcctgga gggcaaaatc aagccccacc tgatgagcca ggagctgccg | 1500 |
| gaggactggg acaagcagcc tgtcaaggtg cttgttggga agaactttga agacgtggct | 1560 |
| tttgatgaga aaaaaaacgt cttttgtggag ttctatgccc catggtgtgg tcactgcaaa | 1620 |
| cagttggctc ccatttggga taaactggga gagacgtaca aggaccatga aacatcgtc | 1680 |
| atcgccaaga tggactcgac tgccaacgag gtgaggccg tcaaagttca tagcttcccc | 1740 |
| acactcaagt tctttcctgc cagtgccgac aggacgtca ttgattacaa cggggaacgc | 1800 |
| acgctggatg ttttaagaa attcctggag agcggtggcc aggatggggc agggatgat | 1860 |
| gacgatctcg aggacctgga agaagcagag gagccagaca tggaggaaga cgatgatcag | 1920 |
| aaagctgtga agatgaact gtaa | 1944 |

<210> SEQ ID NO 27
<211> LENGTH: 513
<212> TYPE: PRT
<213> ORGANISM: Artificial Sequence
<220> FEATURE:
<223> OTHER INFORMATION: SYNTHETIC PEPTIDE

<400> SEQUENCE: 27

Met Lys Lys Val Val Asn Ser Val Leu Ala Ser Ala Leu Ala Leu Thr
1               5                   10                  15

Val Ala Pro Met Ala Phe Ala Ala Pro Glu Glu Glu Asp His Val Leu
            20                  25                  30

-continued

```
Val Leu Arg Lys Ser Asn Phe Ala Glu Ala Leu Ala Ala His Lys Tyr
            35                  40                  45

Leu Leu Val Glu Phe Tyr Ala Pro Trp Cys Gly His Cys Lys Ala Leu
 50                  55                  60

Ala Pro Glu Tyr Ala Lys Ala Ala Gly Lys Leu Lys Ala Glu Gly Ser
65                   70                  75                  80

Glu Ile Arg Leu Ala Lys Val Asp Ala Thr Glu Glu Ser Asp Leu Ala
                85                  90                  95

Gln Gln Tyr Gly Val Arg Gly Tyr Pro Thr Ile Lys Phe Phe Arg Asn
               100                 105                 110

Gly Asp Thr Ala Ser Pro Lys Glu Tyr Thr Ala Gly Arg Glu Ala Asp
            115                 120                 125

Asp Ile Val Asn Trp Leu Lys Lys Arg Thr Gly Pro Ala Ala Thr Thr
        130                 135                 140

Leu Pro Asp Gly Ala Ala Ala Glu Ser Leu Val Glu Ser Ser Glu Val
145                 150                 155                 160

Ala Val Ile Gly Phe Phe Lys Asp Val Glu Ser Asp Ser Ala Lys Gln
                165                 170                 175

Phe Leu Gln Ala Ala Glu Ala Ile Asp Asp Ile Pro Phe Gly Ile Thr
            180                 185                 190

Ser Asn Ser Asp Val Phe Ser Lys Tyr Gln Leu Asp Lys Asp Gly Val
        195                 200                 205

Val Leu Phe Lys Lys Phe Asp Glu Gly Arg Asn Asn Phe Glu Gly Glu
    210                 215                 220

Val Thr Lys Glu Asn Leu Leu Asp Phe Ile Lys His Asn Gln Leu Pro
225                 230                 235                 240

Leu Val Ile Glu Phe Thr Glu Gln Thr Ala Pro Lys Ile Phe Gly Gly
                245                 250                 255

Glu Ile Lys Thr His Ile Leu Leu Phe Leu Pro Lys Ser Val Ser Asp
            260                 265                 270

Tyr Asp Gly Lys Leu Ser Asn Phe Lys Thr Ala Ala Glu Ser Phe Lys
        275                 280                 285

Gly Lys Ile Leu Phe Ile Phe Ile Asp Ser Asp His Thr Asp Asn Gln
    290                 295                 300

Arg Ile Leu Glu Phe Phe Gly Leu Lys Lys Glu Glu Cys Pro Ala Val
305                 310                 315                 320

Arg Leu Ile Thr Leu Glu Glu Glu Met Thr Lys Tyr Lys Pro Glu Ser
                325                 330                 335

Glu Glu Leu Thr Ala Glu Arg Ile Thr Glu Phe Cys His Arg Phe Leu
            340                 345                 350

Glu Gly Lys Ile Lys Pro His Leu Met Ser Gln Glu Leu Pro Glu Asp
        355                 360                 365

Trp Asp Lys Gln Pro Val Lys Val Leu Val Gly Lys Asn Phe Glu Asp
    370                 375                 380

Val Ala Phe Asp Glu Lys Lys Asn Val Phe Val Glu Phe Tyr Ala Pro
385                 390                 395                 400

Trp Cys Gly His Cys Lys Gln Leu Ala Pro Ile Trp Asp Lys Leu Gly
                405                 410                 415

Glu Thr Tyr Lys Asp His Glu Asn Ile Val Ile Ala Lys Met Asp Ser
            420                 425                 430

Thr Ala Asn Glu Val Glu Ala Val Lys Val His Ser Phe Pro Thr Leu
        435                 440                 445
```

-continued

```
Lys Phe Phe Pro Ala Ser Ala Asp Arg Thr Val Ile Asp Tyr Asn Gly
    450             455             460

Glu Arg Thr Leu Asp Gly Phe Lys Lys Phe Leu Glu Ser Gly Gly Gln
465             470             475             480

Asp Gly Ala Gly Asp Asp Asp Leu Glu Asp Leu Glu Glu Ala Glu
            485             490             495

Glu Pro Asp Met Glu Glu Asp Asp Gln Lys Ala Val Lys Asp Glu
            500             505             510

Leu
```